United States Patent
Buchine et al.

(10) Patent No.: US 9,199,037 B2
(45) Date of Patent: Dec. 1, 2015

(54) PORTABLE DRUG MIXING AND DELIVERY SYSTEM AND METHOD

(71) Applicants: Brent Alan Buchine, Watertown, MA (US); Christopher John Stepanian, Somerville, MA (US); Adam Standley, Boston, MA (US)

(72) Inventors: Brent Alan Buchine, Watertown, MA (US); Christopher John Stepanian, Somerville, MA (US); Adam Standley, Boston, MA (US)

(73) Assignee: Windgap Medical, Inc., Somerville, MA (US)

( * ) Notice: Subject to any disclaimer, the term of this patent is extended or adjusted under 35 U.S.C. 154(b) by 0 days.

(21) Appl. No.: 14/218,355

(22) Filed: Mar. 18, 2014

(65) Prior Publication Data

US 2014/0276385 A1 Sep. 18, 2014

Related U.S. Application Data

(60) Provisional application No. 61/917,943, filed on Dec. 19, 2013, provisional application No. 61/800,014, filed on Mar. 15, 2013.

(51) Int. Cl.
*A61M 5/19* (2006.01)
*A61M 5/20* (2006.01)
*A61M 5/315* (2006.01)

(52) U.S. Cl.
CPC ............... *A61M 5/19* (2013.01); *A61M 5/2033* (2013.01); *A61M 5/31596* (2013.01); *A61M 2005/202* (2013.01); *A61M 2005/206* (2013.01)

(58) Field of Classification Search
CPC ................. A61M 2005/202; A61M 2005/206; A61M 5/19; A61M 5/2033; A61M 5/31596
See application file for complete search history.

(56) References Cited

U.S. PATENT DOCUMENTS

| 2002/0049407 | A1 | 4/2002 | Hill |
| 2009/0171311 | A1* | 7/2009 | Genosar et al. ............... 604/411 |
| 2011/0092906 | A1 | 4/2011 | Bottger |
| 2013/0274707 | A1 | 10/2013 | Wilmot |

FOREIGN PATENT DOCUMENTS

WO WO 2012090168 * 7/2012

* cited by examiner

*Primary Examiner* — Imani Hayman
(74) *Attorney, Agent, or Firm* — Ascentage Law, PLLC; Travis L. Johnson; David S. Einfeldt

(57) ABSTRACT

A portable auto-injector configured to store various wet and dry medicament components separately. Wherein prior to injection the various medicaments within the portable auto-injector are mixed through a multi-stage process in one or more chambers within the portable auto-injector. The various chambers being connected by corresponding fluidic channels.

19 Claims, 25 Drawing Sheets

PORTABLE DRUG MIXING AND DELIVERY SYSTEM AND METHOD

CROSS-REFERENCE TO RELATED APPLICATIONS

This application claims the benefit of U.S. Patent Application 61/800,014 filed on Mar. 15, 2013 and U.S. Patent Application 61/917,943 filed on Dec. 19, 2013, which are incorporated herein by reference.

FIELD OF THE INVENTION

The present invention relates generally to auto-injectors and prefilled syringes and more particularly to auto-injectors that store in a compact state and allow for formation or reconstitution of the drug.

BACKGROUND OF THE INVENTION

Individuals who suffer from certain medical conditions are often required to keep an auto-injector or prefilled syringe nearby in order to address a medical need. A few examples of this are insulin pens for people with diabetes, EPIPENS for those with food and insect stings allergies, and antidotes for soldiers at risk of exposure to chemical and/or biological toxins in the field. For example, an allergic reaction may occur in a location physically distant from the nearest hospital or medical facility. For example, bee stings, are more likely to occur outside than indoors. Food containing peanuts are more likely to be supplied to the individual away from a controlled home environment like at a baseball park. Having a portable epinephrine auto-injector nearby enables emergency intervention after an exposure to an allergen.

Size is an issue when it comes to auto-injectors. Many owners of the devices do not carry it with them and a compact device may make it more likely that they will. Common epinephrine auto injector case sizes are about 6 inches by 1½ inches by 1 inch, making them difficult to carry without a secondary carrying device like a purse and/or backpack and/or other container.

SUMMARY OF THE INVENTION

It has been recognized that if a drug can be kept out of the liquid phase and stored as a dry medication, the shelf-life, temperature susceptibility may increase allowing the efficacy and potency of the drug to endure longer and through harsher environments.

It has been recognized that a smaller drug delivery device than a conventional epinephrine auto-injector, which could be attached to a key chain and/or easily fit in a person's pocket, would make the device easier to carry and more likely that the user will have it on their person when needed. An example of such a device package, purely for the purpose of comparison, could be sized similarly to that of a USB "thumb drive" which is designed to be with users on a fairly constant basis. For example, an auto-injector device embodiment has dimensions of 3 inches by 1 inch by ½ inch. However, dimensions of an auto-injector device may vary.

A portable auto-injector is capable of moving from a compact state where the auto-injector is in a shape easier to transport than in an activation state wherein the auto-injector has been extended and/or made larger and/or longer and/or easier to handle in some way. In some embodiments a safety limits movement of the needle assembly and prevents premature needle sticks. The drug is stored in one or more dry and/or wet medicament states until needed.

In an embodiment of a drug mixing system, the system has a movable body in fluid communication with a first and second chamber. The first chamber is configured to store a wet component. The system has an actuation device configured to cause the movable body to enter a portion of the first chamber during a first actuation process and a second chamber during a second actuation process. The movable body as it enters the first chamber forces a wet component through a fluidic channel and into the second chamber. Fluidic communication may enabled with the first chamber and the fluidic channel through a one-way valve, burst membrane, orifice or other mechanism and opening.

For example, the force of the movable body entering into a portion of the first chamber is sufficient to cause fluid communication (such as opening a one-way valve) and allow the wet component stored in the first chamber to flow into the fluidic channel where a dry medicament is stored and cause the dry medicament to combine with the wet component and flows into the second chamber. In a second motion, the movable body moves into the second chamber and forces the combined wet component and dry medicament (now a wet medicament) into a delivery assembly, such as through a needle or jet (needle-less system) and into a subject. One-way fluid communication (as a result of another one-way valve) between the fluidic channel and the second chamber may prevent the wet medicament from flowing back through the fluidic channel when the movable body moves into the second chamber.

In an embodiment of the system, the needle assembly and the second chamber are movable as one unit relative to the housing. In an embodiment, a second actuation device causes a portion of the needle assembly to be expelled outwardly from the housing and into a subject wherein the wet medicament may be delivered through the needle assembly into the tissue, vessel, and/or muscle of the subject.

In an embodiment of the drug mixing system, the movable body has a mixing volume for retaining a dry medicament component. In an embodiment, the movable body has a valve for allowing fluid in one direction from the first chamber into the mixing volume. In an embodiment, the movable body has a valve for allowing fluid in one direction from the mixing volume into the second chamber.

In an embodiment, the movable body has burst valves that allow fluid communication between the mixing volume and the first chamber and the second chamber when required.

In an embodiment of the drug mixing system, the volume of the movable body includes a fluidic channel. In an embodiment the fluidic channel is designed to promote mixing. In an embodiment, the fluidic channel is a micro-fluidic channel.

In an embodiment, the fluidic channel is a tortious path for carrying and/or storing the dry medicament component. In one embodiment, the fluidic channel defines the volume for mixing the wet component with the dry medicament. In an embodiment, the tortious path creates chaotic flow for mixing the wet component with the dry medicament. In an embodiment, the series of structures, walls, or grooves in the walls of the mixer body and or channel help promote mixing of the dry medicament and defining the volume for mixing the wet component with the dry medicament.

In an embodiment, at least one of the dimensions in the channel is less than 2 millimeters. In an embodiment, the Reynolds number in the fluidic channel is less than 2300 causing laminar flow. In an embodiment, the Reynolds number of the laminar flow in the fluidic channel is less than 100. In an embodiment, the Reynolds number in the fluidic channel is less than 10 and in some cases may cause turbulent or chaotic flow. In an embodiment the Reynolds number in the fluidic channel is greater than 2300. In an embodiment, the mixing assembly further includes a plurality of grooves formed therein, wherein the grooves promote mixing when a wet component flows by and/or near the grooves. In an embodiment the mixing assembly further includes bends in the channel wherein the bends promote mixing when a wet component flows by the bends. In an embodiment, the mixing assembly includes obstructions in the flow path wherein said obstructions promote mixing when the wet component flows by the obstructions.

In an embodiment, the movable body has a mixing volume for retaining a dry medicament component prior to mixing with a wet component to form a wet medicament. In an embodiment, the movable body is sized to define a hollow volume sized to the dry medicament component received.

In an embodiment, the second chamber carries a second wet component. The first chamber carries the first wet component to mix with the dry medicament in the fluidic channel disposed in the movable body prior to mixing with the second wet component in the second chamber.

In an embodiment, the second actuation device is a pre-loaded force. In an embodiment, the pre-loaded force is a compression spring. In an embodiment, the second actuation device is activated by the user. In an embodiment, the second actuation device is a torsion spring. In an embodiment, the second actuation device is a torsion spring. In another embodiment an elastic device is used as an actuation device. In another embodiment $CO_2$ cartridges are used. In another embodiment an electronically controlled valves, and chemical driven actuators, compressed gas cylinders, solenoids, electromagnetics, linear motors.

In an embodiment of a drug delivery system, the system has a housing having an extension component that is movable relative to the housing and causing the effective length of the housing to have a larger dimension. The extension component may be a telescoping component, an unfolding component or reattachable component. In one embodiment, the extension component when activated and/or lengthened allows the first actuation device to cause the movable body to move into the first chamber.

In an embodiment, the telescoping component moves laterally relative to the first housing to form the housing having a larger dimension. In an embodiment, the unfolding component rotates about a pivot relative to the housing to form the housing having a larger dimension. In an embodiment, the telescoping component rotates about a longitudinal axis extending through the needle assembly relative to a first and second end of the housing causing the housing to have a larger dimension. In an embodiment, reattachable portion is detached and then reattached to the housing at a different position, thus causing the housing to have a large dimension.

In an embodiment, the system includes a needle assembly in fluid communication with the second chamber and a safety. The needle assembly and the second chamber are movable as one unit relative to the housing. The system has a second actuation device that causes the needle assembly to be exposed or protrude from the housing and capable of injecting a wet medicament formed in the fluidic channel. The safety is movable from a first safety position to a second position prior to the activation of the actuation device.

In an embodiment of the drug delivery system, the system has a needle assembly. The needle assembly and the second chamber are movable as one unit relative to the housing. A second actuation device causes the needle assembly to be exposed or protrude from the housing and capable of injecting a drug formed in fluidic channel that is disposed in the movable body. The movement of the second housing relative to the first housing arms/allows the second actuation device. In an embodiment, the system has a stop for limiting the movement of the second actuation device until triggered.

In an embodiment, the first chamber is collapsible. In an embodiment, the movement of the movable body reduces the volume of the first chamber.

These aspects of the invention are not meant to be exclusive and other features, aspects, and advantages of the present invention will be readily apparent to those of ordinary skill in the art when read in conjunction with the following description, appended claims, and accompanying drawings.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
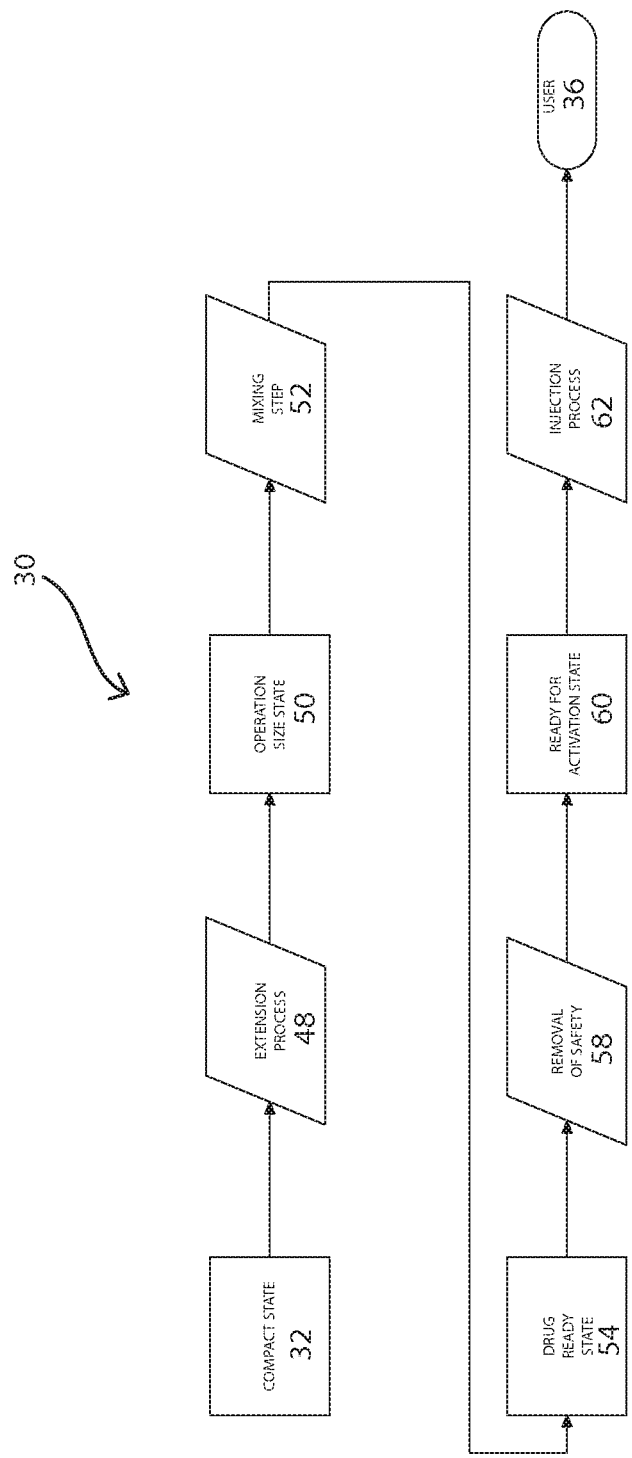
FIG. 1A is a schematic of a method of using a portable auto-injector according to the invention.

A system and method for storing and mixing a dry medicament component with a wet component for delivery to a user. The auto-injector is stored in a compact state where the components of the drug are stored in two or more states that allows for more latitude in storage.

Ease-of-use of an auto-injector becomes critical since it can be sometimes difficult to hold and/or operate a small device. For example, toothbrushes designed for kids are often larger than adult versions in order to make it easier for small hands to grasp. When proposing a small auto-injector this must be taken into consideration since children are likely users of a device that may be needed to save their lives. One way of addressing this would be to produce a device that is small and ultraportable when not in use, but larger when in use.

Referring to FIG. 1, a schematic of a method of using a portable auto-injector 30 is shown. The portable auto-injector 30 is carried by a user in a compact state as represented by block 32. In the compact state 32, a dry medicament, which is going to be delivered to a user 36 (as a wet medicament) is stored separately from wet components, such as a dry medicament 38 and a wet component 40 as shown in FIG. 8A. In addition in the compact state 32, the portable auto-injector 30 is in a safe position where the auto-injector 30 cannot inadvertently stab a user 36 with a needle 46 until desired, as seen in FIGS. 6A-7B and 9F.

The auto-injector 30 is moved from the compact state 32 by an extension process as represented by a parallelogram 48. The extension process 48 can take several forms as explained in further detail below, such as by pulling components relative to each other, rotating components relative to each other, or twisting components relative to each other. With the extension process 48 completed, the auto-injector 30 is of a size that it is comfortable for the user to operate, an operation size state 50.

The housing has a larger dimension in the operation size 50. In one embodiment, the portable auto-injector 30 is 3 inches by 1 inch by 0.5 inches in the compact state 32 and 4½ inches by 1 inch by 0.5 inches in the operation size state 50.

The mixing of the dry medicament and wet components in some embodiments may occur as part of the extension process 48 or another mixing step as represented by a parallelogram 52. The mixing step 52 causes the wet component 40 to pass through and combine with the dry medicament 38 therein forming the wet medicament 34 which is to be delivered to a user 36. The wet medicament ready state is represented by a block 54.

In certain embodiments, the extension process 48 places the auto-injector 30 in condition for use. In the alternative and as represented in FIG. 1A, the portable auto-injector requires a separate and distinct step of removal of a safety step/pre-activation step as represented by a parallelogram 58 to place the auto-injector 30 in the ready for activation state as represented by a block 60.

Still referring to FIG. 1A, with the auto-injector 30 in the ready for activation state 60, the auto-injector 30 can be placed in proximity to the user 36. The injection process step as represented by a parallelogram 62 can be triggered to deliver the drug to the user 36.

It is recognized that the operator of the portable auto-injector 30 and the person receiving the drug 34 can be two distinct persons. For example, the person receiving the wet medicament 34 could be a child or someone in a state in which at they could not operate the auto-injector 30.

Figure 1B:
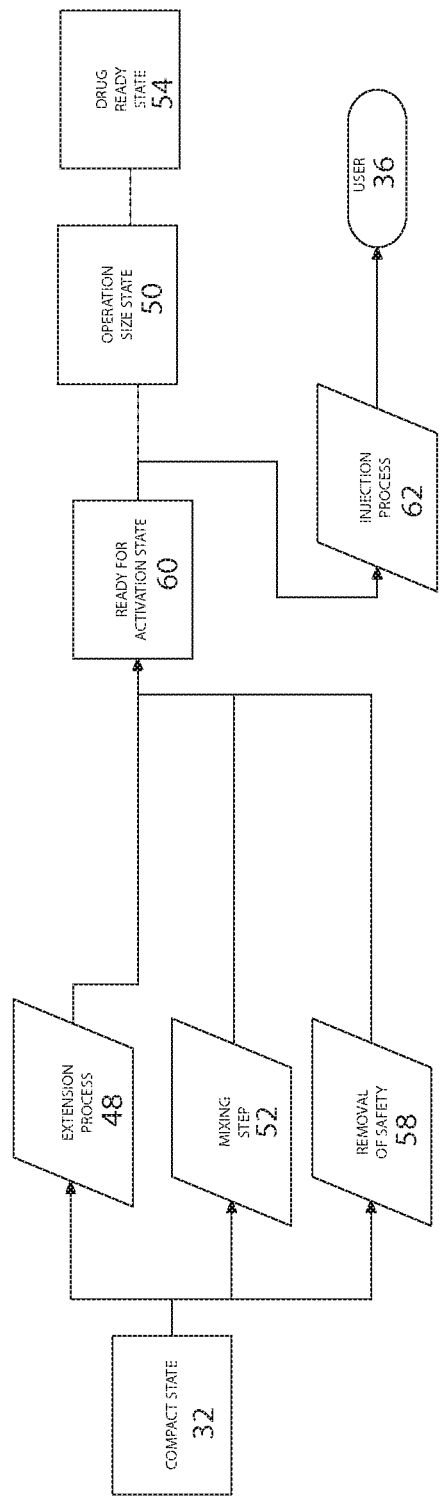
FIG. 1B is a schematic of an alternative embodiment and method of using a portable auto-injector according to the invention.

Referring to FIG. 1B, a schematic of an alternative embodiment and method of using a portable auto-injector 30 is shown. In contrast to the embodiment shown in FIG. 1A, where the extension process 48, the mixing step 52, and the removal of the safety 58 occur at separate and distinct steps, the process of extending the components to the operation size state 50 accomplish other steps. For example the extension process 48 also causes the mixing step 52. The mixing step 52 causes the wet component 40 to pass through and combine with the dry medicament 38 therein forming the wet medicament 34 which is going to be delivered to a user 36.

In addition, the extension process 48 also results in the removal of the safety 58 therein placing the auto-injector 30 in the ready for activation state as represented by a block 60.

In FIG. 1B, the operation size state block 50 and the drug ready state block 54 are shown adjacent to the ready for activation state 60, the desired state. In certain embodiments, the drugs may be in a ready state in the compact state 32 (i.e., there is no mixing of a wet component 40 with a dry medicament 38 to form the wet medicament 34 after the portable auto-injector 30 is shipped to the user in that the wet medicament 34 is already mixed.) In certain embodiments, the auto-injector 30 does not have separate components associated with the safety.

Still referring to FIG. 1B, with the auto-injector 30 in the ready for activation state 60, the auto-injector 30 can be placed in proximity to the user 36. The injection process step as represented by the parallelogram 62 can be triggered to deliver the drug to the user 36.

Figure 2C:
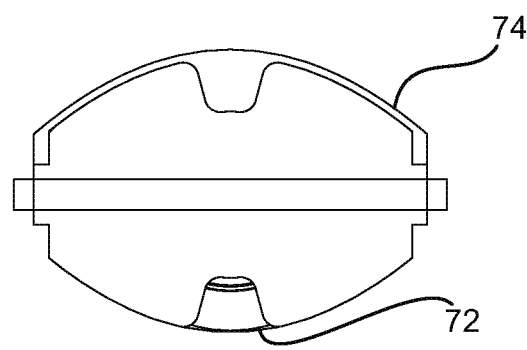
FIG. 2C is a top view of the portable auto-injector 30 in the compact/storage position.
Figure 2A:
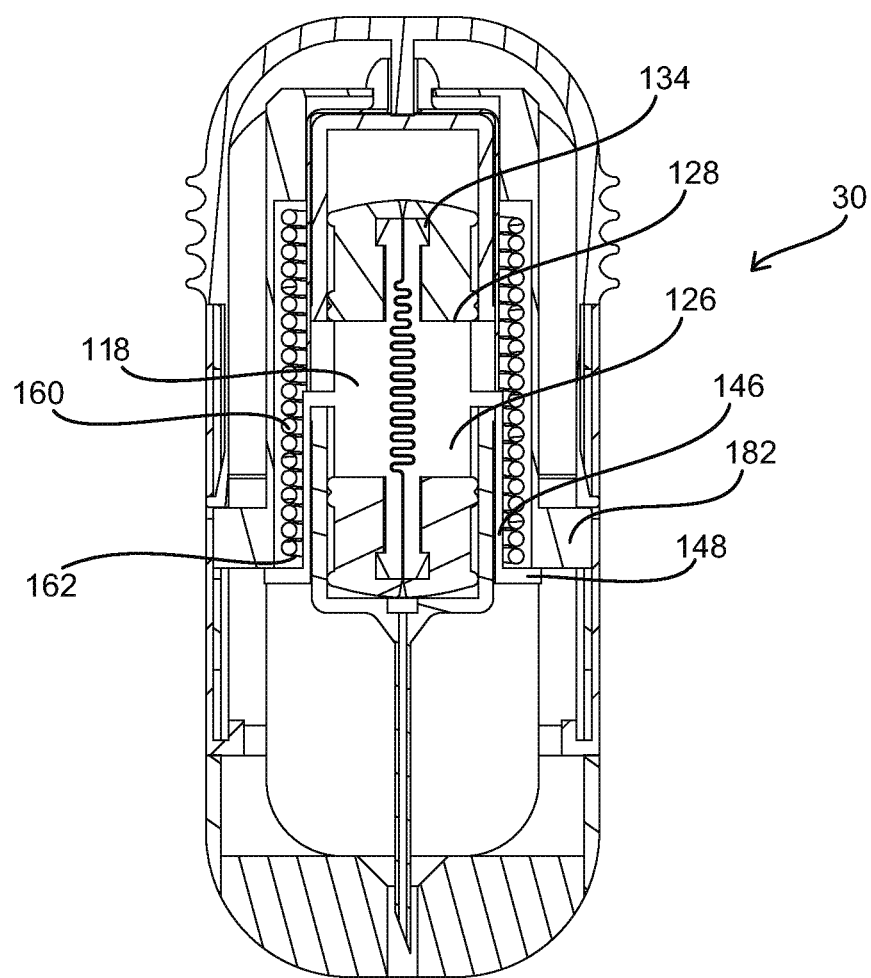
FIG. 2A is a front sectional view of a portable auto-injector 30 in a compact/storage position 22.

Referring to FIG. 2A, a front sectional view of a portable auto-injector 30 in a compact/storage position 32 is shown. The auto-injector 30 has a series of components including a housing 70 having a top shell 72 and a bottom shell 74 as best seen in FIG. 2C which shows the top view of the portable auto-injector 30 in the compact/storage position 32 and FIG. 2B which shows a side sectional view of the portable auto-injector 30 in the compact/storage position 32.

Figure 3A:
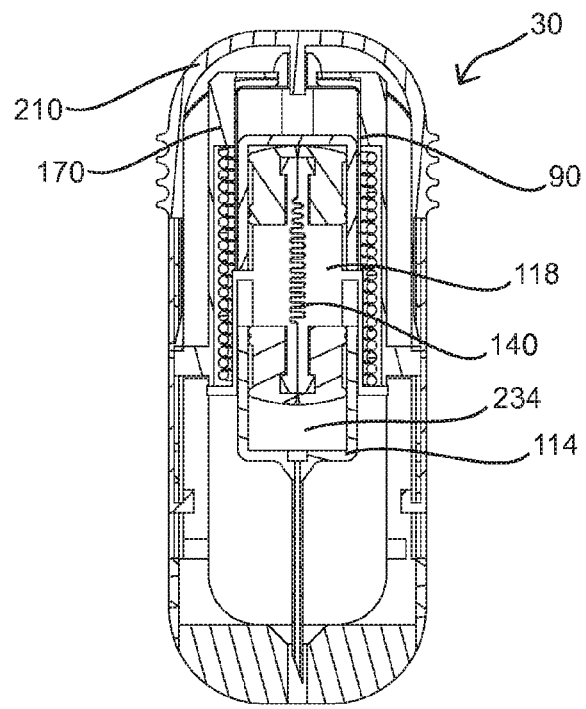
FIG. 3A is a front sectional view of the portable auto-injector 30 in the extension position.
Figure 3B:
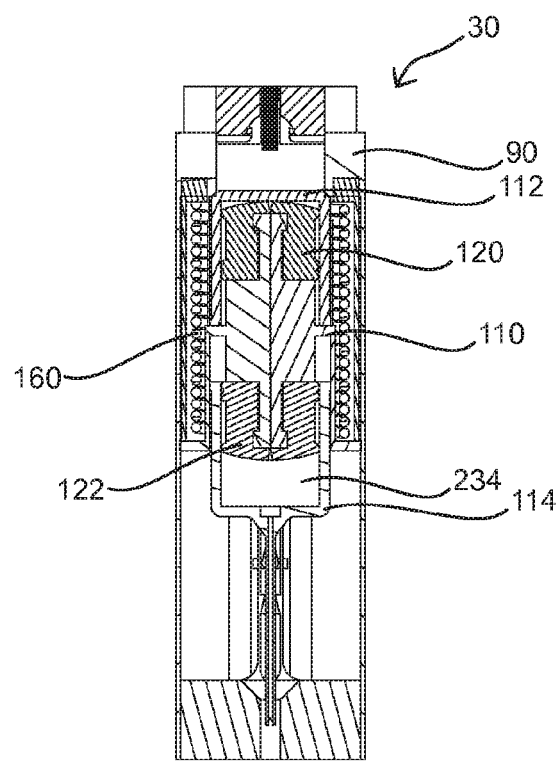
FIG. 3B is a side sectional view of the portable auto-injector 30 in the extension position.

The housing 70 has a pair of side walls (not labeled) each having a plurality of grooves that engage components of an extender slide 90 for retaining the extender slide 90 in the compact state 32 as seen in FIGS. 2A and 2C and the operation state 50, as seen in FIGS. 3A and 3B. In addition, the housing 70 has a plurality of detents and stops that interact with components of an injector 100 for retaining it in the compact state and the operation state. The extender slider 90 is held into place by split fingers after an actuation latch member is pulled through the split fingers and the split fingers retain their position while the latch member is supported on the split fingers.

The portable auto-injector 30 has a wet/dry component combining system 110. The wet/dry component combining system 110 has a pair of vials 112 and 114. The first vial 112 holds the wet component 40 when the auto-injector 30 is in the compact state 32. The second vial 114 is connected to a needle assembly 116 that includes the injection needle 46 and stores the wet medicament 34 prior to delivery as further described below. The wet/dry component combining system 110 has a movable body 118 with a fluidic channel disposed therein and a pair of plungers 120 and 122. The first plunger 120 interacts with the first vial or chamber 112 and the second plunger 122 interacts with the second vial or chamber 114. In another embodiment, first plunger 120 and second plunger 122 and movable body 118 with fluidic channel are all made of one piece of material. In another embodiment, these are separate assemblies. In another embodiment 118 simply creates a fluid path from vial 112 to vial 114.

Figure 8A:
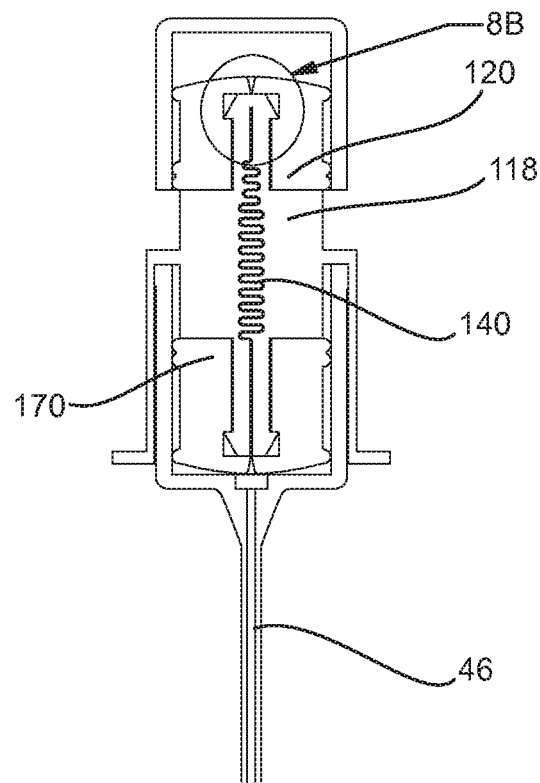
FIG. 8A is an enlarged view of the drug delivery portion of the portable auto-injector.
Figure 8B:
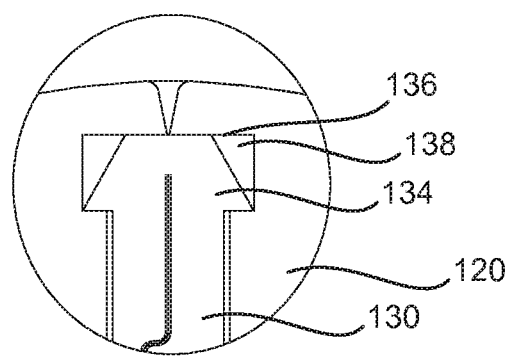
FIG. 8B is an enlarged view of the plunger membrane interface.

The movable body 118 with a fluidic channel 140 is interposed between the two vials 112 and 114 and the two plungers 120 and 122. The movable body 118 with a fluidic channel has a cylindrical body 126 and a pair of parallel ends 128. The movable body 118 with a fluidic channel 140 has a pair of posts 130 and 132. A post 130 and 132 extends from each of the parallel ends 128. Each post 130 and 132 has an enlarged tip 134 for engaging the walls 136 of a void 138 in one of the plungers 120 and 122 as best seen in FIG. 8B. The movable body 118 with a fluidic channel may include a single fluidic channel 140 that extends from the first post 130 to the second post 132. The movable body 118 has an annular ring 146 with a lip 148. The lip 148 interacts with a first end 162 of a compression spring 160.

The compression spring 160 has a second end 164 that interacts with an intra-housing 170 that has a base 172 and an annular ring 174 that encircles the compression spring 160. The base 172 of the intra-housing 170 has an annular lip 178 that engages the second end 164 of the compression spring 160. The base 172 has a hole 180. The intra-housing 170 has a pair of tabs 182. Each tab 182 is interposed between a split finger 186 of the injector 100 as best seen in FIG. 2D.

The intra-housing 170 is connected to the extender slide 90. The two components move together in lateral movement from the compact state 32 to the operation size state 50. The extender slide 90 is the component that a user can grab to move the auto-injector 30 to the operation size state 50.

Figure 2B:
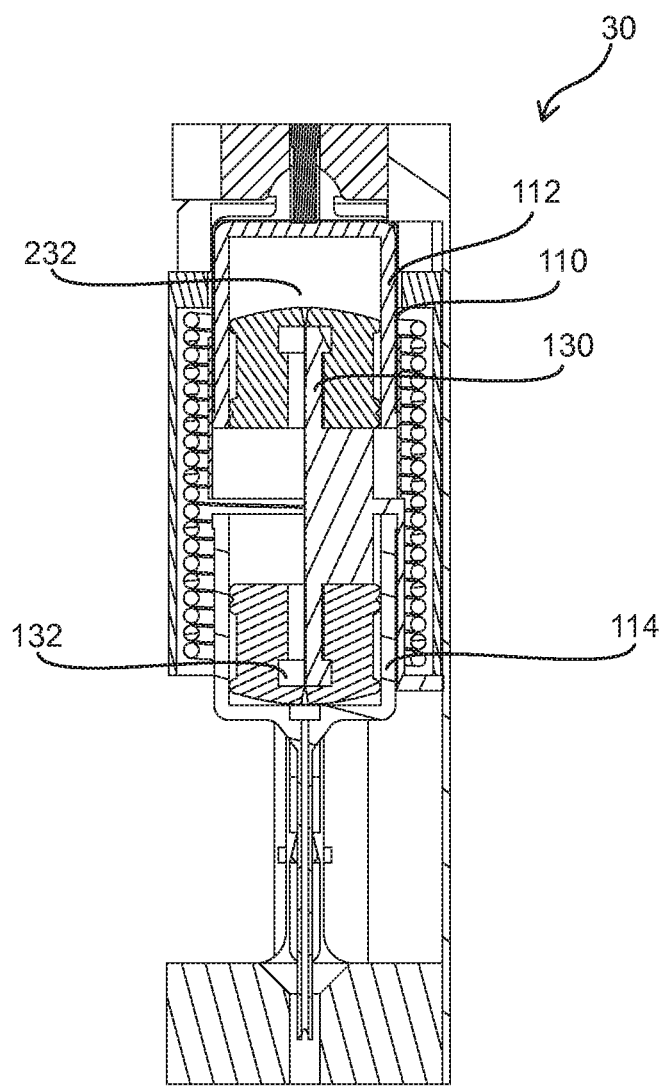
FIG. 2B is a side sectional view of the portable auto-injector 30 in the compact/storage position 22 of FIG. 2A.
Figure 2D:
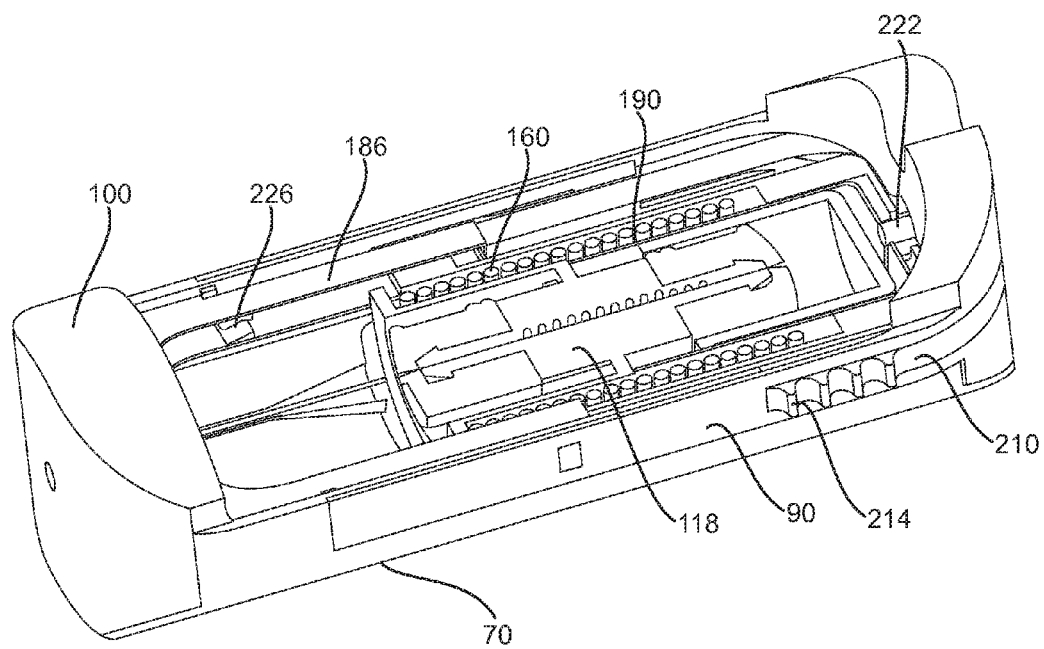
FIG. 2D is a perspective view of the portable auto-injector in the compact/storage position with portions broken away.

Still referring to FIGS. 2A and 2B, the portable auto-injector 30 has a drug delivery movement ring 190. The drug delivery movement ring 190 has a base 192 with a stub 194 that projects through the hole 180 in the intra-housing 170. The stub 194 has a slot 196 that extends across the stub 194 which creates a pair of legs that can flex as explained below. The stub has a hole 198 that extends through the slot 196. The stub 194 has a lip 200 that engages the outer surface of the base of the intra-housing 170 so the drug delivery movement ring 190 moves with the intra-housing 170.

The portable auto-injector has a safety 210. The safety 210 has a U-shape with a pair of legs 212. Each leg 212 has a series of knurls 214 to facilitate the user moving the safety 210 from a safe position as seen in FIGS. 2A-3B, to an activation position as seen in FIGS. 4A-6D and explained below. In addition, each leg 212 has a detent 216 that extends through an opening 218 in the extender slide 90 to hold the safety 210 in the safe position. The base 220 of the U-shaped safety 210 has a pin 222. The pin 222 of the safety 210 extends into the hole 198 of the stub 194 of the drug delivery movement ring 190.

Figure 4A:
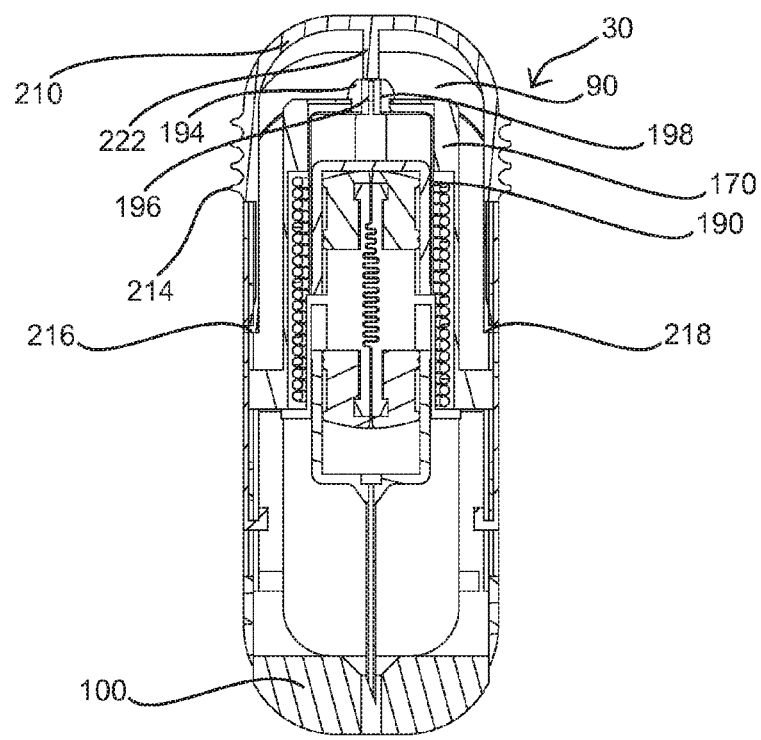
FIG. 4A is a front sectional view of the portable auto-injector 30 with the safety extracted.
Figure 4B:
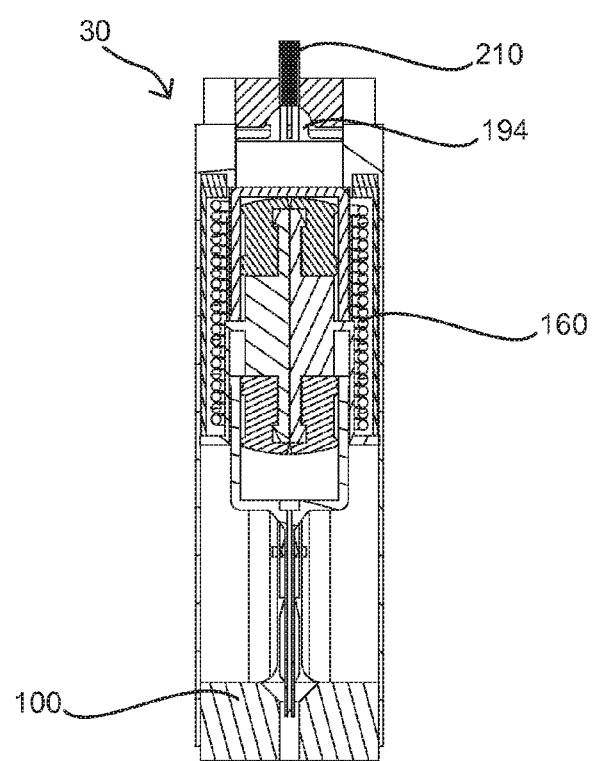
FIG. 4B is a side sectional view of the portable auto-injector 30 with the safety extracted.

Referring to FIG. 2D, a perspective view of the portable auto-injector 30 in the compact/storage position 32 with portions broken away is shown. The safety 210 is received in a groove within the extender slide 90. The detent 216 of the safety 210 can be seen extending through the opening 218 in the extender slide 90 to hold the safety 210 in the safe position. The series of knurls 214 project beyond the surface of the adjacent extender slide 90 to facilitate the user moving the safety 210 from the safe position as seen in FIG. 2D to the activation position as seen in FIGS. 4A-4B. The pin 222 of the safety 210 is shown extending through the hole 198 of the stub 194 of the drug delivery movement ring 190.

The compression spring 160 is seen extending from the first end 162 where it engages the lip 148 of the annular ring 146 of the movable body 118 to the second end 164 where it engages the annular lip 174 of the base 172 of the intra-housing 170. One of the tabs 182 of the intra-housing 170 is shown between one of the pair of split fingers 186 of the injector 100. In addition, a drive block 226 is shown on the split finger 186 of the injector 100.

The base of the extender slide 90 has a slot to receive a rib on the housing 70 to maintain alignment.

Referring to FIG. 3A, a front sectional view of the portable auto-injector 30 in the operation size state 50 is shown. A side sectional view of the portable auto-injector 30 in the operation size state 50 is shown in FIG. 3B. As the extender slide 90 moves in the extension process 48 to the operation size state 50, the intra-housing 170, the safety 210, and the drug delivery movement ring 190 also moves. The movement of the drug delivery movement ring 190 causes the mixer 118 of the drug mixing system 110 to move upward. This upward movement forces the first plunger 120 to move upward in the first vial 112 therein reducing the volume in the first vial 112; the volume is referred to as a first chamber 232. This decrease in volume in the first vial 112 causes the wet component 40 to be forced through a hollow volume, the micro channel or fluidic channel 140 in the movable body 118 that may contain a dry medicament. As the first plunger 120 moves into the first vial 112, the second plunger 122 is moving out of the second vial 114 therein creating a volume, a second chamber 234, to receive the wet medicament 34 created by the mixing of the wet component 40 with the dry medicament 38 in the fluidic channel 140.

In this embodiment, the extension process 48 and the mixing step 52 occurs concurrently; this is in contrast to the two distinct steps as described with respect to FIG. 1A. The mixing of the wet component 40 with the dry medicament 38 is described with respect to FIGS. 8A and 8B.

Referring to FIG. 4A, a front sectional view of the portable auto-injector 30 with the safety 210 extracted is shown. A side sectional view of the portable auto-injector 30 with the safety 210 extracted is shown in FIG. 4B. As indicated above, the intra-housing 170 and the drug delivery movement ring 190 move with the extender slide 90. The user engages the knurls 214 on the safety 210 moving the safety 210 to the ready for activation state 60. The pair of detents 216 that were held in the openings 218 of the extender slide 90 are forced out of the openings 218 and flex inward by the movement of the safety 210 upward.

The movement of the safety 210 results in the injector 100 moving downward after a bump trigger forces together stub 194 into a bump groove, which is possible after the safety (and a pin portion of the safety) is removed. This forcing together of the stub 194 allows it to fall back through the aperture and releases the stored energy in the compression spring, thus driving the injector out of the housing and into a user or subject. The bump groove may be shaped in a conical or similar shape having an angle(s) that put pressure on the outside of objects and push them inward as the object is forced into the groove. Usually the objects are stubs that won't pass through apertures or holes without pressing the nubs or sides of the stubs allowing them to fit through the aperture or opening.

While the process is referred to as the removal of the safety 58, the safety 210 is still connected to the rest of the auto-injector. The movement of the safety 210 results in the pin 222 being extracted from the hole 196 in the stub 194. With the pin 222 removed from the stub 194, the stub 194 can flex inward into the space occupied by the slot 198. The lip 200 of the stub 194 is no longer engaging the base 192 of the drug delivery movement ring 190 so the entire stub 194 can push through the hole 180 in the base of the intra-housing 170 as seen in FIGS. 6A and 6B. However prior to the movement of the drug delivery movement ring 190 relative to the intra-housing, the injector 100, which has been driven downward as described above, needs to be move back up relative to the housing 70 as described below with respect to FIGS. 5A and 5B.

Figure 5A:
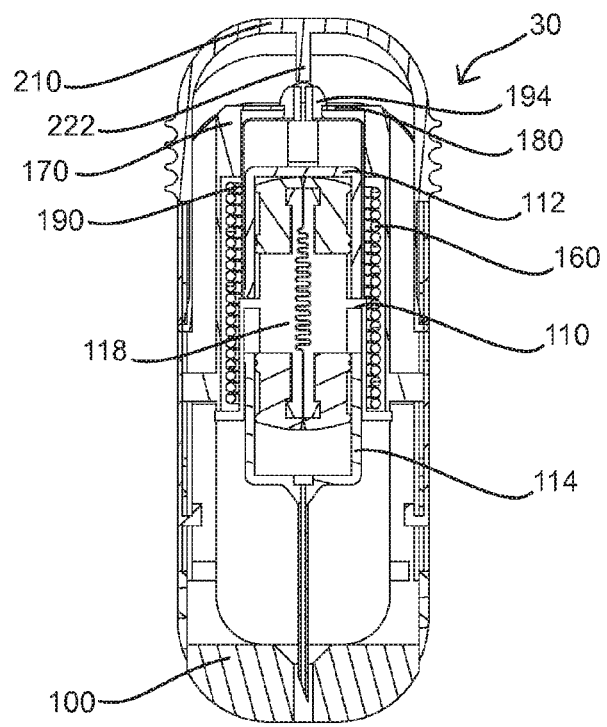
FIG. 5A is a front sectional view of the portable auto-injector 30 in an injection position with the trigger pushed down.
Figure 5B:
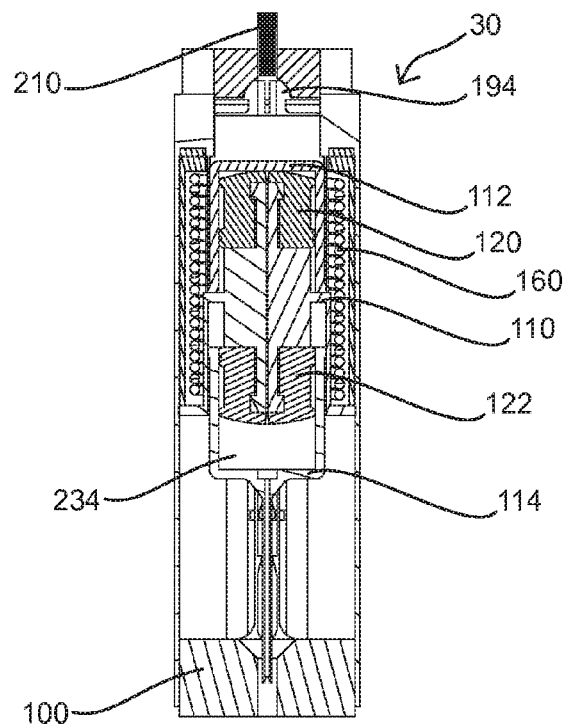
FIG. 5B is a side sectional view of the portable auto-injector 30 in the injection position with the trigger pushed down.
Figure 6A:
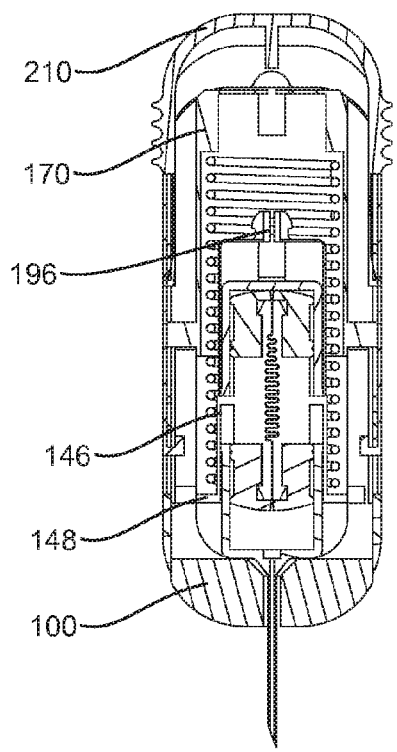
FIG. 6A is a front sectional view of the portable auto-injector 30 in injecting position.
Figure 6B:
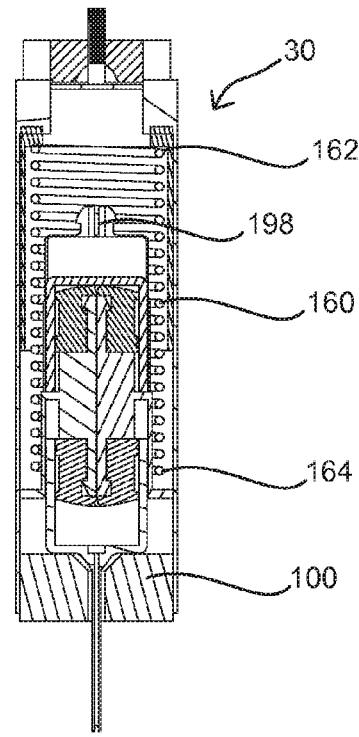
FIG. 6B is a side sectional view of the portable auto-injector 30 in injecting position.

Referring to FIG. 5A, a front sectional view of the portable auto-injector 30 in an injection position with the trigger pushed down is shown. A side sectional view of the portable auto-injector 30 in the injection position with the trigger pushed down is shown in FIG. 5B.

Referring to FIG. 6A, a front sectional view of the portable auto-injector 30 in the injecting position is shown. A side sectional view of the portable auto-injector 30 in the injecting position is shown in FIG. 6B. The movement of the injector 100 upward back into the housing 70 results in the intra-housing 170 moving upward relative to the drug delivery movement ring 190.

In that the pin 222 of the safety 240 is no longer in the hole 198 of the stub 194, the stub 194 can flex. The stub 194 flexes, filling the space of the slot 196 therein allowing the lip 200 to pass through the hole 180 in the base 172 of the intra-housing 170. The lip 148 of the annular ring 146 of the movable body 118, which is engaged by the second end 164 of the compression spring 160, is forced downward. This force moves the movable body 118 and the drug delivery movement ring 190 downward.

The compression spring 160 continues to push the lip 148 of the annular ring 146 of the movable body 118 with fluidic channel 140 downward. The needle 46 is driven downward through an opening in the injector 100. The needle 46 is driven until the second vial 114 engages the injector 100.

Figure 7A:
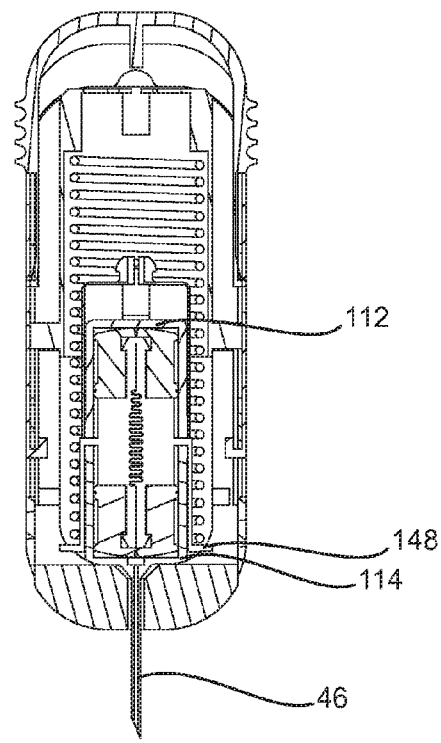
FIG. 7A is a front sectional view of the portable auto-injector 30 in a drug delivery position.
Figure 7B:
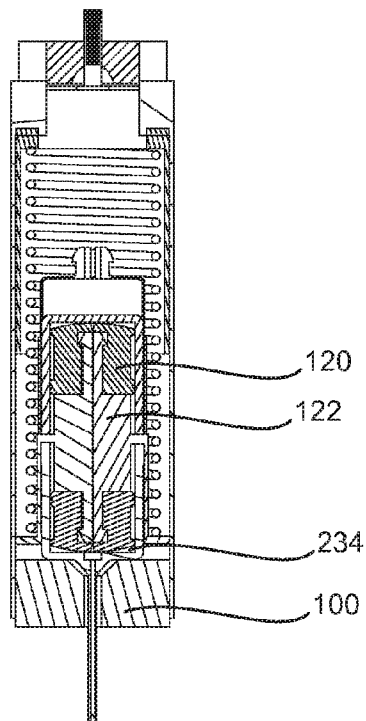
FIG. 7B is a side sectional view of the portable auto-injector 30 in the drug delivery position of FIG. 7A.

Referring to FIG. 7A, a front sectional view of the portable auto-injector 30 in a drug delivery position is shown. A side sectional view of the portable auto-injector 30 in the drug delivery position is shown in FIG. 7B. The compression spring 160 continues to push the lip 148 of the annular ring 146 of the movable body 118 with fluidic channel 140 downward causing the mixer 118 and the plungers 120 and 122 to move relative to the vials 112 and 114 and in particular the second vial 114 forcing the drug 34 out of the second chamber 234 within the second vial 114 through the needle 46 into the user 36.

Referring to FIG. 8A, an enlarged view of the drug mixing system 110 of the portable auto-injector 30 is shown. As indicated above, the movement of the movable body 118 with fluidic channel and the two plungers 120 and 122 relative to the vials 112 and 114 occurs at different times in the operation. In the embodiment described with respect to FIG. 1A, the mixer 118 and the two plungers 120 and 122 move at a time distinct from the extension process 48 of the portable auto-injector 30. In the embodiment described with respect to FIGS. 2A-7B, the movement of the movable body 118 and the two plungers 120 and 122 to combine the wet medicament 34 occurs with the extension process 48 into the operation size state 50. In both cases, the movable body 118 and the two plungers 120 and 122 move again relative to the vials 112 and 114 to move the wet medicament 34 out of the second vial 114 by reducing the second chamber 234. The wet medicament 34 is forced through the needle 46 which is driven by the compression spring 160 just prior to the movable 118 with fluidic channel 140 and the two plungers 120 and 122 move again relative to the vials 112 and 114.

Still referring to FIG. 8A, the wet/dry combining system 110 in one embodiment has first vial 112 and the second vial 114 made of glass and/or biocompatible plastic and/or metal and/or any other acceptable material and or other materials acceptable by a regulatory body (such as the FDA) or other approved bodies. The first chamber 232 of the first vial 112 is where the liquid solution, the wet component 40, for dissolving (reconstituting, holding in solution) the dry medicament is stored. In one embodiment the solution may contain water for injection. In one embodiment the solution can be pH optimized with a buffer to enable dissolution. In one embodiment the buffer can be an acid or a base. In one embodiment the buffer can be HCl. In one embodiment, the solution can contain other additives and preservatives, like NaCl, metabisulfite, or others. The first plunger 120 is inserted into the first vial 112; the movement of the first plunger 120 defines the size, the volume, of the first chamber 232.

The second vial 114 starts out empty in the embodiments discussed above; the second chamber 234 essentially has no volume when the auto-injector is in the compact state 32 as seen in FIGS. 2A-2D. It is recognized that the second vial 114 may be designed and sized such that the second chamber 234 has a volume sufficient to contain a liquid such as a pH adjusting solution, which in one embodiment can be water for injection. In another embodiment the pH adjusting solution can contain a buffer. In another embodiment the neutralizing agent may be an acid. In another embodiment the neutralizing agent can be a base. In another embodiment a neutralizing agent could be sodium hydroxide. The second plunger 122 is inserted in the second vial 114. Thus a method of quickly dissolving a dry medicament in a buffer solution, which is later pH adjusted in a second solution in the second chamber and suitable for injecting into a person allows for a quick and compact drug mixing and delivery solution that can have a greater shelf-life and be less susceptible to environmental factors. A neutralizing agent may be used. A buffer may be comprised of an acid and a base.

In the embodiments shown above, the movable body 118 with fluidic channel 140 stores the dry medicament 38. A dry medicament storage assembly (also called the microfluidic assembly) in one embodiment has no microfluidic channels but contains the dry medicament 38. In another embodiment, it has at least fluidic and/or one microfluidic channel. In another embodiment it has more than one fluidic or microfluidic channel. In another embodiment a dry medicament 38 is stored inside at least one fluidic and/or microfluidic channel. In another embodiment a dry powder medicament is stored outside the fluidic and/or microfluidic channel while still being contained within the dry medicament storage assembly. In another embodiment a liquid is stored inside the microfluidic or fluidic channel and is forced out by another liquid. In another embodiment different liquid medicaments and/or dry medicaments are stored in a plurality of microfluidic channels inside the microfluidic assembly. In another embodiment, some of the microfluidic channels are in fluid communication with each other. In another embodiment, at least two microfluidic channels are in fluid communication with each other. In another embodiment, none of the microfluidic channels are in fluid communication each other, except for they may all empty into a shared vial or chamber.

Referring to FIG. 8B, in an embodiment one or both of the plungers 120 and 122 contain an orifice and/or burst membrane 244 or sealed structure and/or valve that may break and/or move and/or open and/or create fluid communication between the first vial 112 and the movable body 118, the microfluidic assembly, and/or fluid communication between the second vial 114 and the microfluidic assembly upon the action of extending the device. The placement of the orifice and/or burst membrane 244 is dependent on the embodiment and the particular medicament and drug.

In the portable auto-injector 30, the needle assembly 116 extends from the second vial 114. In the embodiment shown, the injector 100 prevents the needle 46 from premature needle sticks. However, the end of the injector 100 can be covered to maintain the sterility of the needle 46. It is recognized that in certain embodiments, the needle assembly 116 contains a needleless drug delivery mechanism. In one embodiment the needle is covered with a rubber protective barrier which may be used to prevent contamination from entering the needle when the injector is stowed and not in use.

Referring to FIGS. 9A-9F, illustrations of an alternative portable auto-injector in various positions is shown. In this embodiment the auto-injector 30, the first vial 112 is narrower and longer than the second vial 114 therein making the portable auto-injector slightly longer in the stowed compact state and also adding hydraulic assistance to fluid flow from the first vial 112 into the second vial 114 which makes the action of extending the injector easier to accomplish. Hydraulic assistance is created by narrowing the vial and making it longer, thus giving extra throw in order to exchange fluid volumes between vials.

Figure 9A:
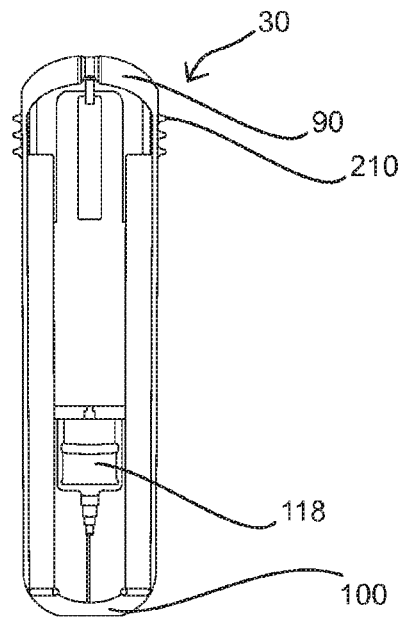
FIGS. 9A-9F are illustrations of an alternative portable auto-injector in various positions.

The portable auto-injector 30 is shown in the compact/storage position in FIG. 9A. It is unable to make an injection in this condition. This is the condition where it may be carried and stored until ready for use.

Figure 9B:
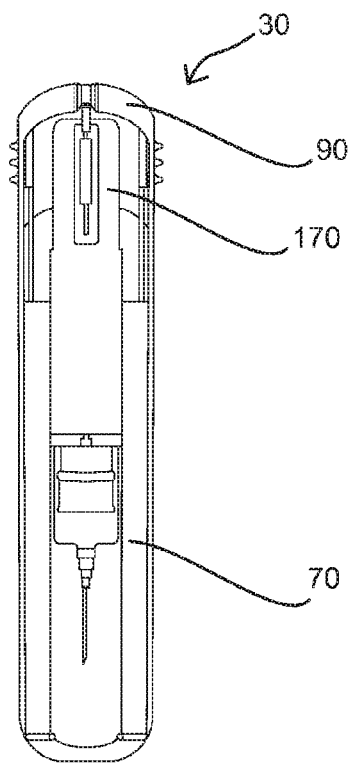

Referring to FIG. 9B, the portable auto-injector in the extended/drug ready position is shown. The moving of the extender, the extender slide 90, upward results in the outer pin and the inner pin being extended together; the outer pin is similar to the intra-housing 170 and the inner pin is similar to the drug delivery movement ring 190 in the embodiment described with relation to FIGS. 2A-7B. This action causes the first plunger 120 to move upward into the first vial 112 in a way that creates a build-up of pressure in the first vial forcing the sealing device 244, such as an orifice and/or seal and/or or membrane and/or valve, as best seen in FIG. 8B, to move and/or change in some way in order to create fluid communication between the first vial 112 and the movable body 118, comprising a dry medicament storage assembly. As the movable body 118 and the plungers 120 and 122 move relative to the vials 112 and 114, the volume of the second vial 114, the second chamber 234, increases in size. The movable body 118, the dry medicament storage assembly, is in fluid communication with the second vial 114. The solution, the wet component 40, in the first vial 112 begins to flow into the dry medicament storage assembly, the movable body 118, dissolving the dry powder into a liquid or wet medicament, the dry medicament 38, and then flowing into the second vial 114.

In this state, the extended auto-injector becomes longer making the auto-injector easier to grip. The dissolved liquid medicament and/or partially dissolved medicament is transferred into the second vial 114 and stored until the next step is initiated.

Figure 9C:
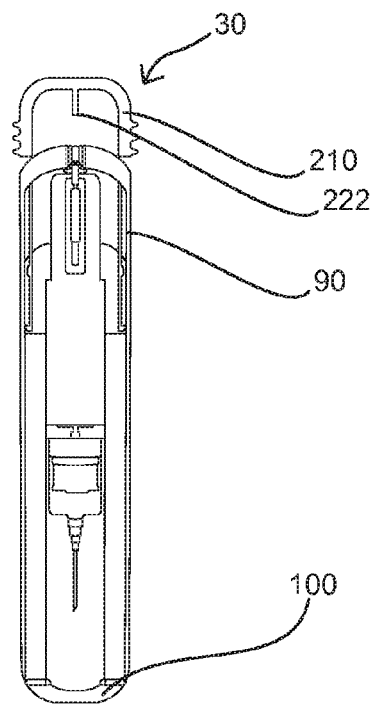

Referring to FIG. 9C, the portable auto-injector 30 in the ready for activation state with the safety removed is shown. After the inner pin has stopped moving as seen in FIG. 9B, the needle assembly housing is resting on the split fingers and needle assembly housing stops. The safety 210 can extend further outward and/or be completely removed as shown in FIG. 9C. The outward movement of the safety 210 results in the safety pin being removed from the stub, which was previously prevent the firing or unloading of the compression spring. A bump switch allows the user or administrator to push on the needle injection side of the injector, which pushes the stub into the bump groove and allows the stub to slide through the hole releasing the stored energy in the compression spring. The released energy forces the needle assembly into the person as well as movable body into the second vial, thus forcing the wet medicament through the needle assembly into the person. While the safety 210 is shown as slid upward, it is recognized that in some embodiments the safety 210 can removed entirely from the portable auto-injector 30. In the same step the trigger extends out from the device on the injection side making the injector ready for injection.

Figure 9D:
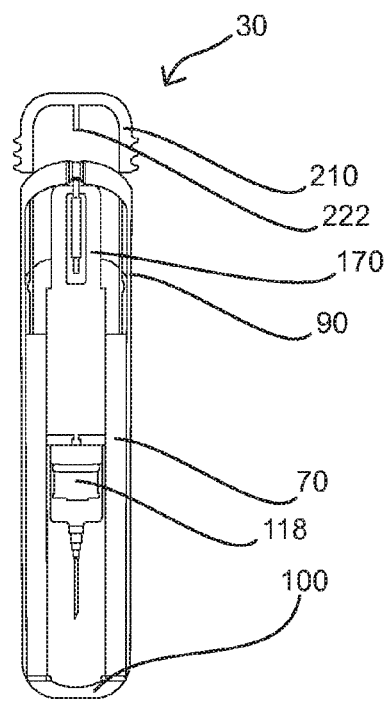
Figure 9E:
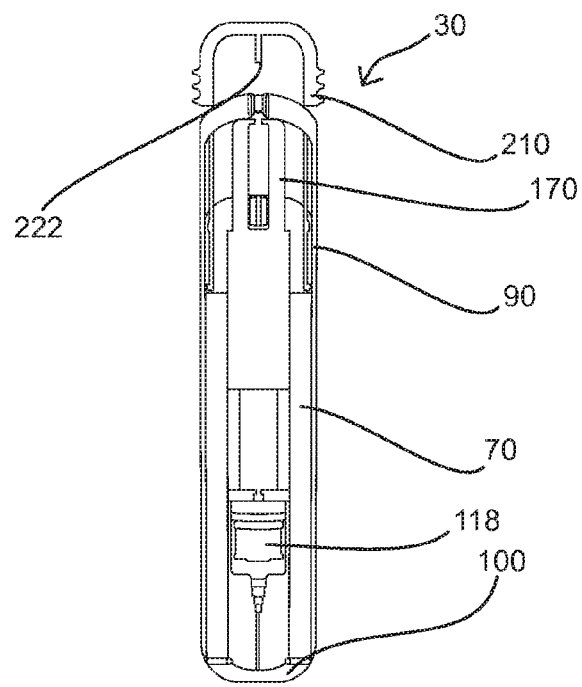
Figure 9F:
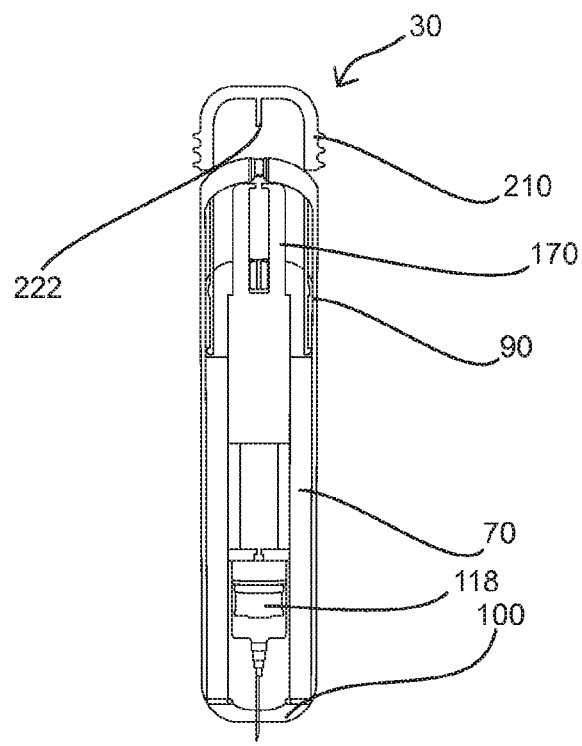

Referring to FIG. 9D, the portable auto-injector 30 in a pre-trigger position is shown. In this position, the bump trigger 100 can be pressed causing the needle assembly to rise forcing the bump switch to pinch together. The bump switch becomes smaller allowing it to clear a hole. The needle assembly then ejects, as seen in FIG. 9E under the force of a spring pushing the needle into a human and/or non-human. The spring continues to apply force, which then forces the liquid into the body as seen in FIG. 9F.

Figure 10A:
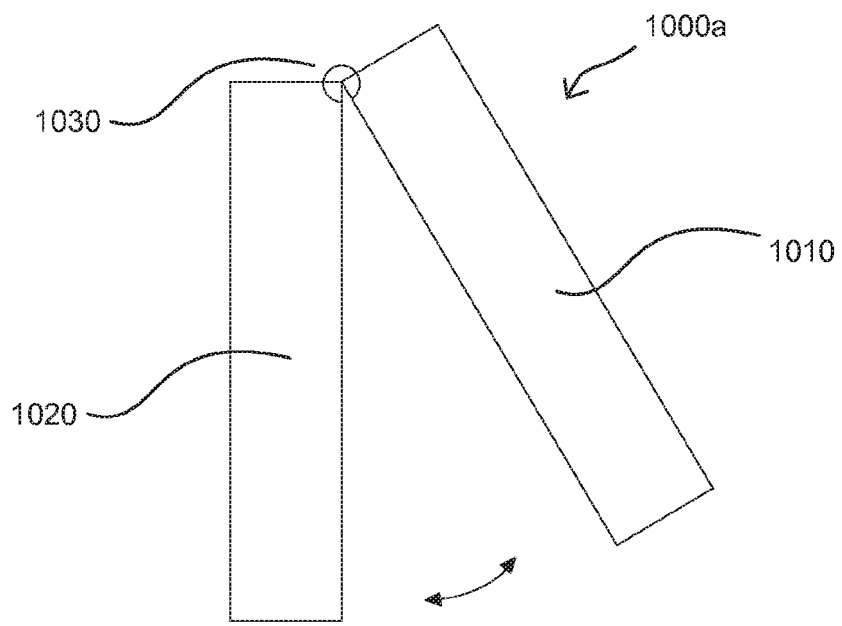
FIG. 10A is a front sectional view of an alternative pivotable portable auto-injector in the compact position.
Figure 10B:
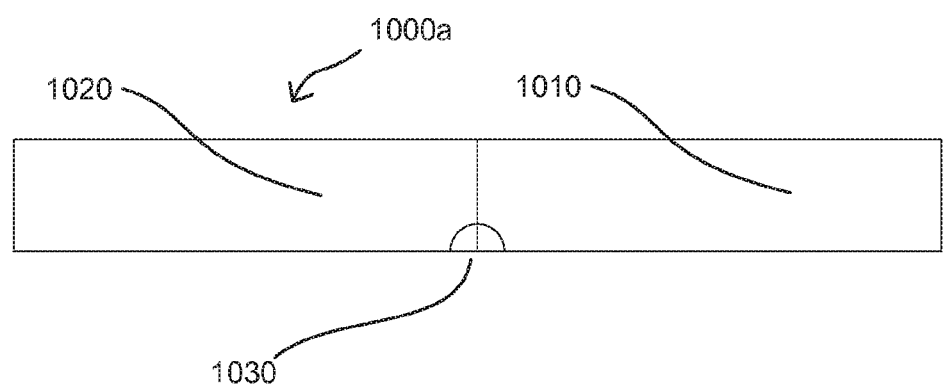
FIG. 10B is a front sectional view of the alternative pivotable portable auto-injector of FIG. 10A in the extended position.

Referring to FIG. 10A, a front sectional view of an alternative pivotable portable auto-injector 1000 in the compact position is shown. Similar to the previous embodiments, the portable auto-injector 100 has a wet/dry combining system 110 and an injector 100. In contrast to the previous embodiments, the auto-injector 1000 does not go from a compact state to the extended state by pulling an extender in a longitudinal direction. In this embodiment, the auto-injector 1000 has a flip design that has an upper housing 1010 that rotates relative to a lower housing 1020 about a hinge point 1030. In this embodiment, the upper housing 1010 contains a drive mechanism that moves the components of the wet/dry combining system 110 located in the lower hosing. FIG. 10D shows the auto-injector 1000 in the extended state.

Figure 10C:
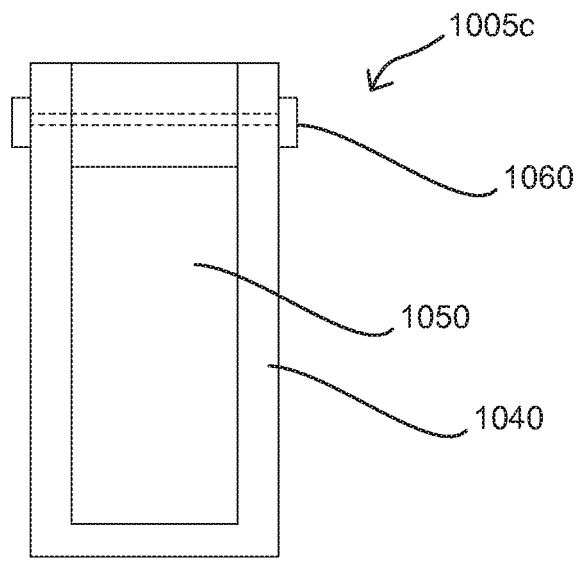
FIG. 10C is a front sectional view of another alternative pivotable portable auto-injector in the compact position.
Figure 10D:
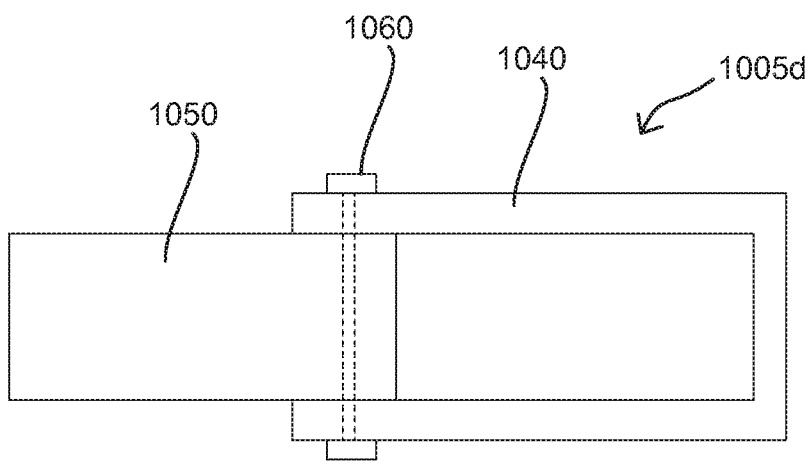
FIG. 10D is a front sectional view of the alternative pivotable portable auto-injector of FIG. 10C in the extended position.

Referring to FIG. 10C, a front sectional view of an alternative pivotable portable auto-injector 1005 in the compact position is shown. Similar to the previous embodiments, the portable auto-injector 100 has a wet/dry combining system 110 and an injector 100. In this embodiment, the auto-injector 1005 has an outer housing 1040 that rotates relative to an inner housing 1050 about a pivot point 1060. FIG. 10D shows the auto-injector 1005 in the extended state.

Figure 11A:
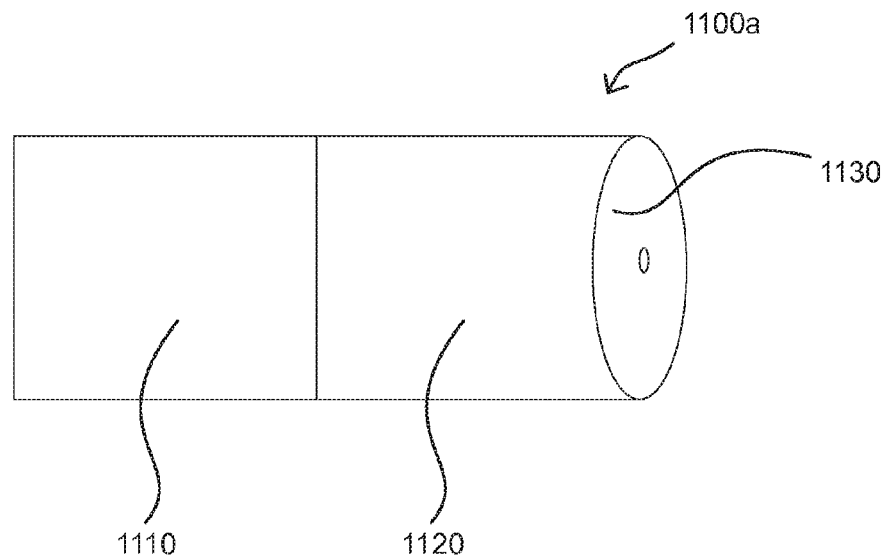
FIG. 11A is a front sectional view of an alternative twist portable auto-injector in the compact position.
Figure 11B:
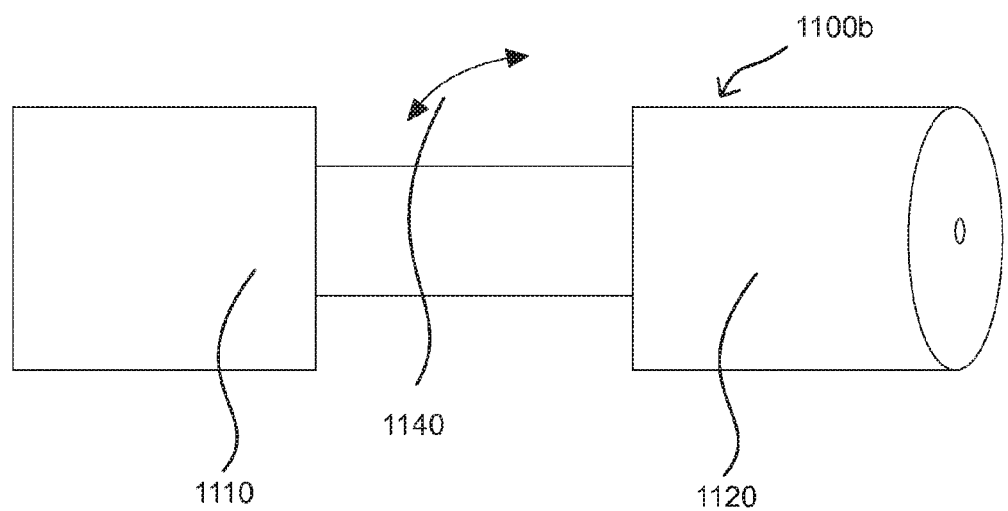
FIG. 11B is a front sectional view of the alternative twist portable auto-injector in the extended position.

Referring to FIG. 11A, a front sectional view of an alternative twist portable auto-injector 1100 in the compact position is shown. In this embodiment, the auto-injector 1100 has an upper housing 1110 and a lower housing 1120. The two housings 1110 and 1120 are rotated relative to each other to allow the housings 1110 and 1120 to move apart through a central telescoping shaft 1140. FIG. 11B shows the twist portable auto-injector 1100 in the extended position. The movable body 118 in the wet/dry component combining system 110 is shown with one micro channel 140 in the embodiment discussed with respect to FIGS. 2A-7B. It is recognized that the wet/dry component combining system 110 can having multiple conduits or channels and seals. The mixing assembly allows for two different types of medicaments (or two doses of the same) to be mixed and inserted into a person using a single needle or other delivery system. A seal can span the orifices of each storage cavity which are each in fluid communication with a different channel contained within the mixing device.

These channels may vary in length and size enabling a time mixing/release of each medicament. For example, a first wet component is stored in a unique channel(s) that has a pathway shorter than the unique channel(s) in which the second wet component are stored in and are in fluid communication with. The first wet component mixes with the first dry component, homogenizes (in this embodiment, but not all embodiments), enters the needle assembly and is injected into a person, where the second wet component takes longer to mix with the second dry component and follows after the first mixed medicament has entered the needle assembly to be injected into the person. This is useful for two medicaments that are not compatible to be stored in the same portions of the mixing assembly and/or reconstituted or mixed together in the same channel.

Microfluidic devices or systems enable control and manipulation of fluids at very small scales. At sub-centimeter and/or sub-millimeter dimensions, the role of interfaces starts to become dominate and surface tension, fluidic resistance and such begin to control behavior, which may respond differently than macroscopic properties of fluid flow. For example, a main flow channel is machined in glass or polymer with a series of "herringbone" or other type of grooves, which create an environment causing the flow of material through the channel to induce mixing. These structures and features create a series of eddies, vortices, or folds inside the channel, which function to stir or mix and dissolve dry medicaments into a wet component thus forming a solution.

Embodiment may be made of two parts, such as a machined portion where the main channel and grooves have an alternating pattern (these grooves may also be randomized) are all formed therein. A base that is a flat glass or polymer is then attached to machined portion enclosing the main channel.

Alternatively, the flow channel may be constructed to widen and narrow or bulb/bulge along one side, two sides, or around the entire cross-section of the channel. A microchannel that gets wider and smaller may be useful in inducing mixing within the flow channel. For example, the main channel is initially smaller in width and then expands in width to a swell. The swell in other configurations may act as a reservoir or well and have larger amounts of dry component stored therein. Again the swell may be a larger pocket or open area in which smaller structures may be placed within, the swell and any contained structures therein help cause disruption of flow. Swells or wells may be placed strategically through a micro-channel system to facilitate mixing.

Figure 12:
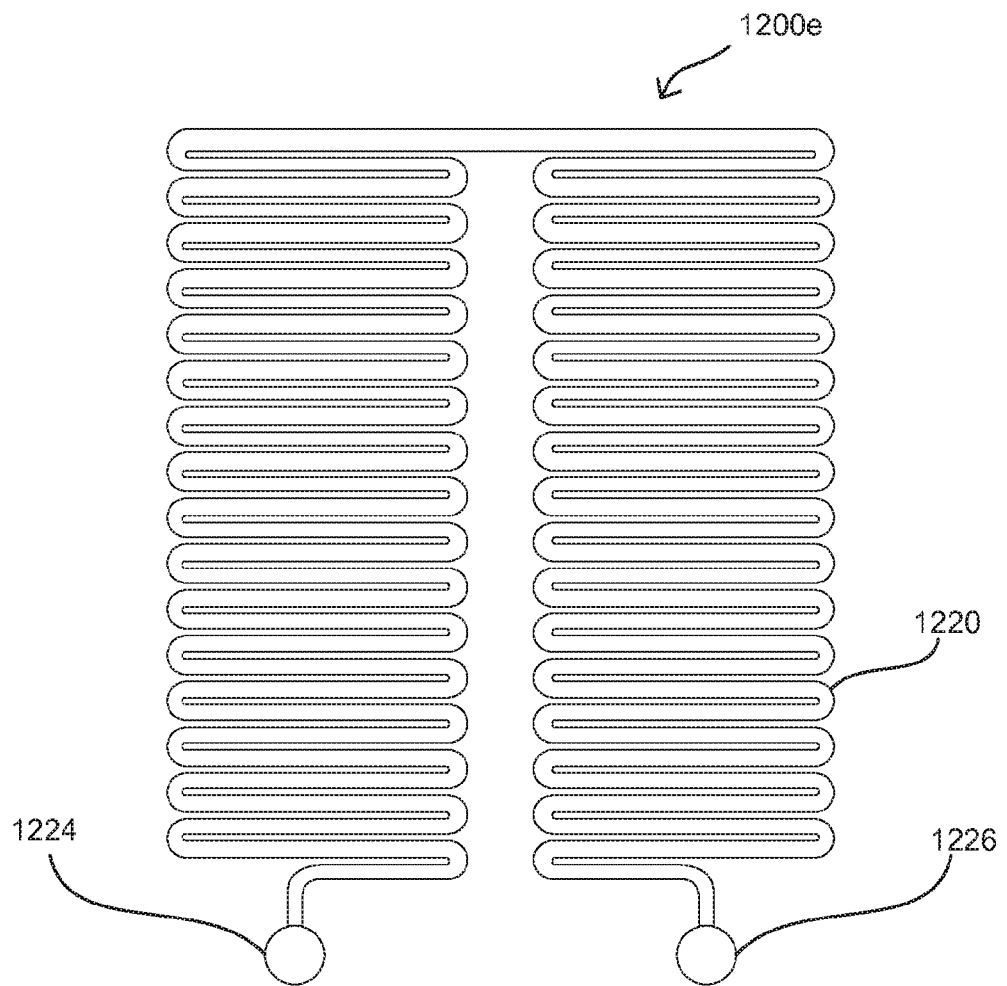
FIGS. 12 and 13 are sectional views of two alternative micro-channels.
Figure 13:
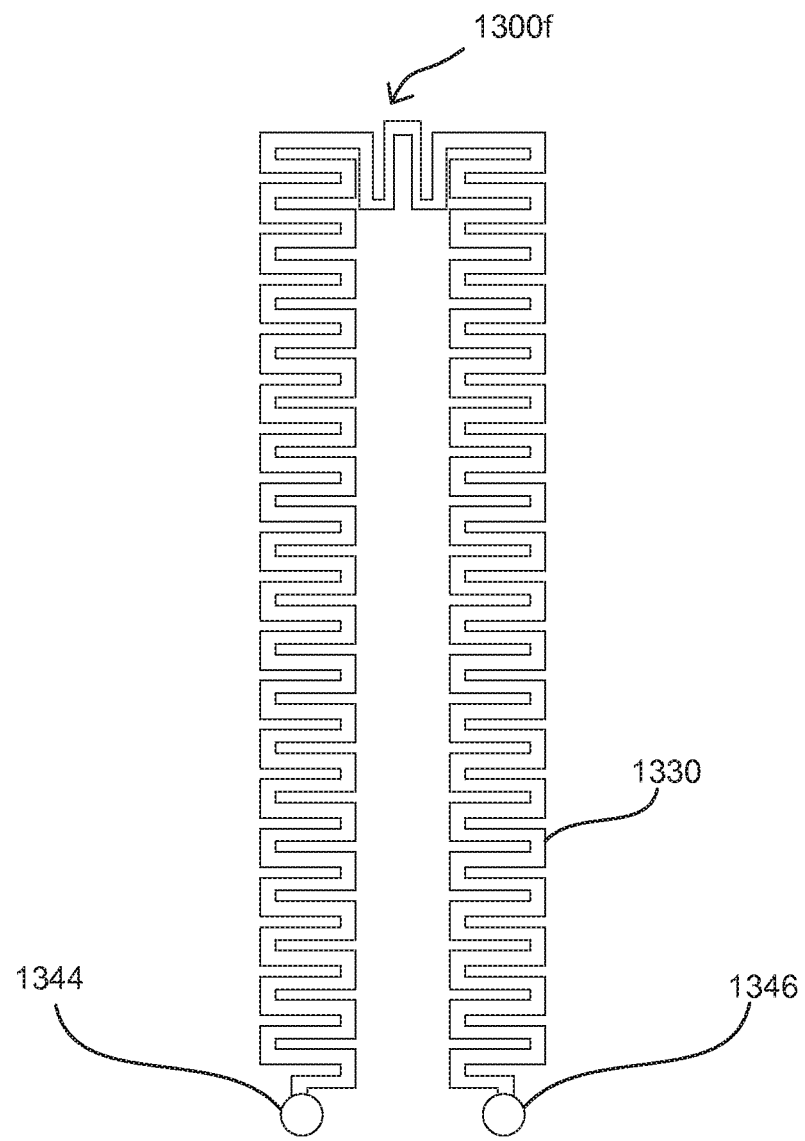

Another way of promoting mixing is to introduce bends or turns into the channels and/or microchannel(s) of the mixing device such as using a serpentine channel shown in FIGS. 12 and 13 rather than a straight channel, varying width, or herringbone design. These serpentines have two functions. First, they enable miniaturization of the plumbing by bending the fluid flow direction so that the channel can double back, thus a longer channel more efficiently utilizes a smaller area. Second, natural flow becomes disrupted every time there is a bend or elbow in the channel, which results in mixing. These serpentine meanders can be designed so there are soft turns 1220 that snake back and forth (shown in embodiment 1200e), or they can be designed with sharp 90 degree bends 1300, which is shown in 1300f. They can even be designed so that the bend exceeds 90 degrees (not shown) that forms a more saw-like tooth pattern. Each embodiment will result in different mixing properties that can enable control over the quantity and quality of mixing. This may be important given that certain drug compounds can be damaged if mixing is too aggressive whereas other compounds may require a more aggressive mixing device. This variability in tuning the mixing conditions allows for a variety of wet/dry components to be used in a compact auto-mixing injector device as control is one key performance attribute of the present application. In each of these microfluidic embodiments 1200e and 1300f each is comprised of a single channel having an opening 1224, 1334 to receive a wet component after the seal has been activated to an open or mixing state and an exit 1226, 1336 configured to be in fluid communication with a needle assembly or an in-between homogenization region.

In another configuration, a straight microfluidic channel configured with parallel walls may be sufficient to mix wet and dry components. Dry components stored inside a portion of the microfluidic channel may act to promote mixing within the channel. When the liquid moves through the channel and begins to push into the dry component contained in a portion therein, the flow front will cause natural turbulence or chaotic flow that focuses the flow towards the center of the channel and then causes the liquid to double back in the reverse direction near the channel wall. In order to make this happen, the channel dimension, which, in one embodiment can be defined by a square cross-section, should be below a certain size. For this embodiment and many of the embodiments described herein, one or both sides of the channel cross-section may have a dimension less than 2 mm, or between 1 mm and 2 mm, or less than 1 mm, or between 500 um and 1 mm, or less than 500 um, or between 250 um and 500 um, or less than 250 um, or between 100 um and 250 um, or less than 100 um, or between 50 um and 100 um, or less than 50 um, or between 10 um and 50 um, or less than 10 um, or between 1 um and 10 um, or less than 1 um. For purposes of this application, channels having a channel with a cross-sectional dimension less than 1 um are considered to be nanofluidic and have their respective set of properties for mixing medicaments.

U.S. patent application Ser. No. 13/529,757 filed on Jun. 21, 2012 and published a published patent application US 2013/0178823 on Jul. 11, 2013 describes additional designs of micro channels and is incorporated herein by reference.

In an embodiment, at least one dimension in the channel is less than 2 millimeters which mixes the dry component 24 into the wet component 26 where the Reynolds number in the diluent is less than 100, relying on chaotic mixing. An example of this could be a series of structures where at least one dimension in the channel is less than 2 millimeters which mixes the dry drug into the diluent where the Reynolds number in the diluent is less than 10, enabling mixing. In some embodiments the dry medicament fully dissolves into the wet component. However, in other embodiments the dry medicament is suspended in the wet component.

It is recognized that the syringe 40 can be replaced by an alternative source of fluid and motive force such as a fluid pump.

In embodiments described above, the actuation force of the auto-injector is supplied by a stored energy source such as the compression spring 160. It is recognized that the energy may also come from user input. For example, when the user telescopes and/or hinges the device, this mechanical action can simultaneously load the auto-injector with the source of energy and put the device in ready mode. A trigger can then be used to discharge the energy source, pushing the needle into the body and delivering a liquid dose of medicament and/or hydrate a powdered medicament into a liquid dose and deliver this medicament into the body of a patient.

It is recognized that this might be enabled with a tension spring that remains in a coiled state before activation. The action of telescoping the injection device may pull the tension spring in such a way to create sufficient potential energy needed to trigger the device, inject the patient, and deliver the medicament.

Another embodiment would be to use a compression spring that is in the extended state before activation. The action of telescoping the injection device may compress the spring in such a way to create sufficient potential energy needed to trigger the device, inject the patient, and deliver the medicament.

Most auto-injectors have a pre-stored energy source, for example, a spring or cartridge of compressed gas. If the safety mechanism fails the injector can accidentally fire in an unintended way. Since this device's actuation force is not pre-stored, there is less risk of an accidental discharge and additional degree of safety.

In the embodiments discussed, a blister or burst membrane are described as one method of separating the wet and dry components. It is recognized that for this device another method of sealing is have the seal moved out of the way when the device becomes activated and/or telescoped. For example, like removing a cork from a wine bottle, the sealing structure can be moved out of the way creating fluid communication between the wet and dry components upon telescoping or flipping open the injector.

It is also recognized that while telescoping or flipping the device, after the seal has been removed or moved out of the way, there can be a force that simultaneously draws or pulls fluid into the dry powdered medicament that results in the reconstitution or hydration of the medicament into a liquid dose. This is slightly different from the pushing of liquid into/through the dry powdered medicament.

In one embodiment the dry medicament is epinephrine. In one embodiment the dry medicament is glucagon. In one embodiment the dry medicament is a clotting factor. In one embodiment the dry medicament is diazepam. In one embodiment the dry medicament is Embrel. In one embodiment the dry medicament is Xolair. In one embodiment the dry medicament is a nerve agent antidote, such as butyrylcholinesterase. In one embodiment the dry medicament is sumatriptan. In one embodiment the dry medicament is a pharmaceutical agent. In one embodiment the dry medicament is a biologic. It may also be a small molecule pharmaceutical agent.

Figure 14A:
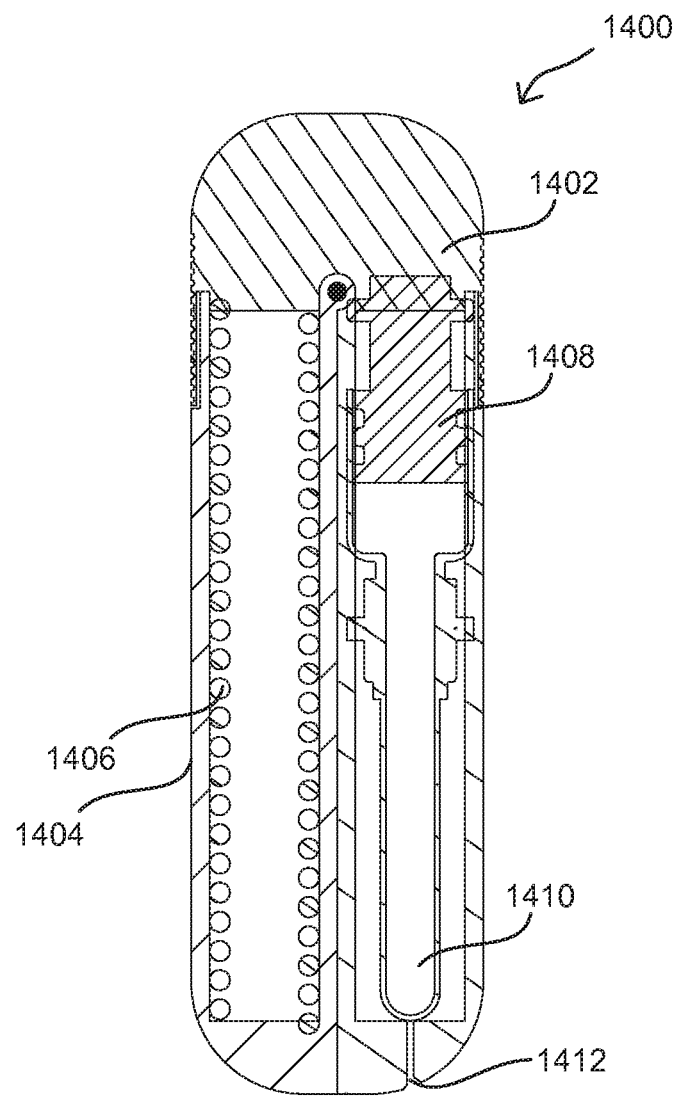
FIGS. 14A-D illustrate an unfolding injector device.
Figure 14B:
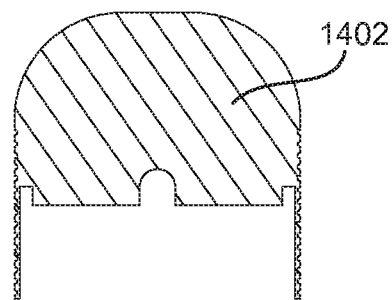
Figure 14C:
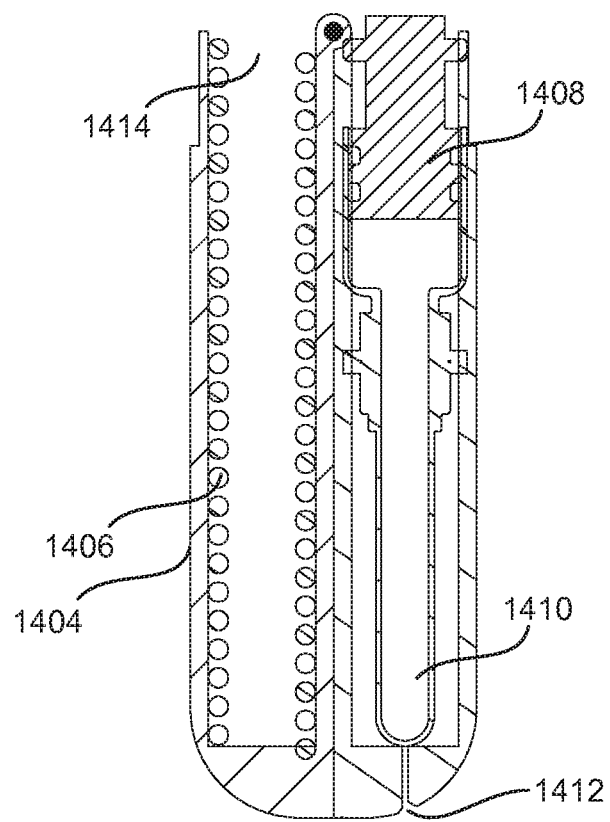
Figure 14D:
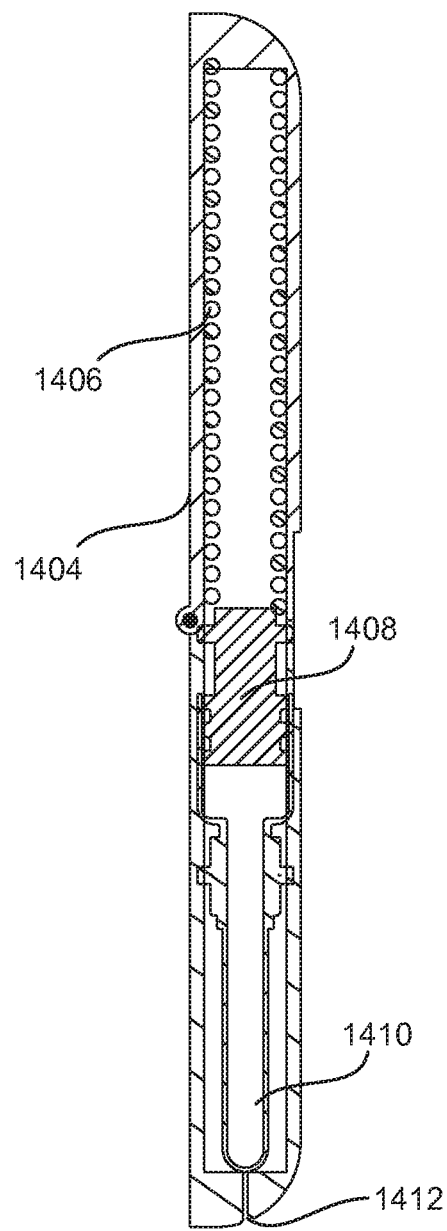

Referring to FIGS. 14A-D illustrate an unfolding injector device. A cross-sectional view of an unfolding mixing and delivery device 1400 is shown. A safety 1402 is positioned one end of 1400 and prevents it from being able to unfold. Upon removal of safety 1402 the housing 1404, which has a preloaded spring 1406 disposed therein, is configured to pivot and elongate the device 1400 as shown in FIG. 14D. Spring 1406 may then engage with a mixing body 1408 that has at least one wet component stored therein and cause it to mix with a dry medicament. For example, as the housing rotates about a hinge the downward pressure on the vial causes the vial to mix with the dry medicament. The mixing assembly is steadied about a ledge prior to downward force of the portion of the housing containing the compressions spring engages the needle and mixing assembly side. The mixing assembly is then actuated as stated as it moves off the ledge and begins combining the wet component from the vial with the dry medicament in the mixing assembly. Similar to the telescoping embodiment above a bump trigger may then cause the preloaded compression spring to engage and cause the needle assembly to protrude from the. The combined wet medicament may then traverse the needle assembly 1410, which upon a second actuation step causes a needle to protrude through opening 1412 and deliver the wet medicament. As discussed elsewhere, the unfolding device may be comprised of various safety's and release mechanisms that allow for a single or multi-step process of mixing the wet and dry components and delivering such into a subject.

Figure 15B:
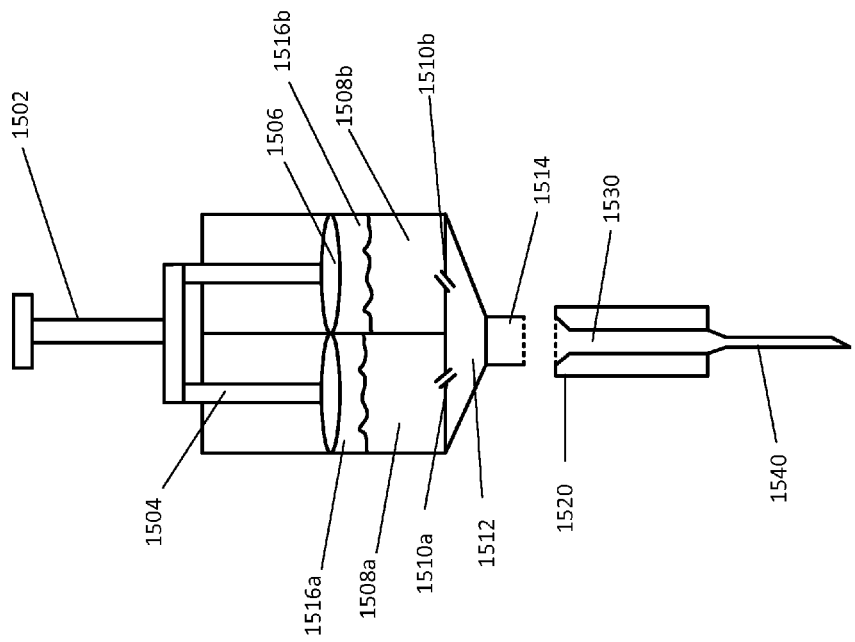
FIGS. 15 A-B illustrate a dual wet chamber injection configured to hold two wet components that combine to aide in dissolving dry medicament in a fluidic channel.
Figure 15A:
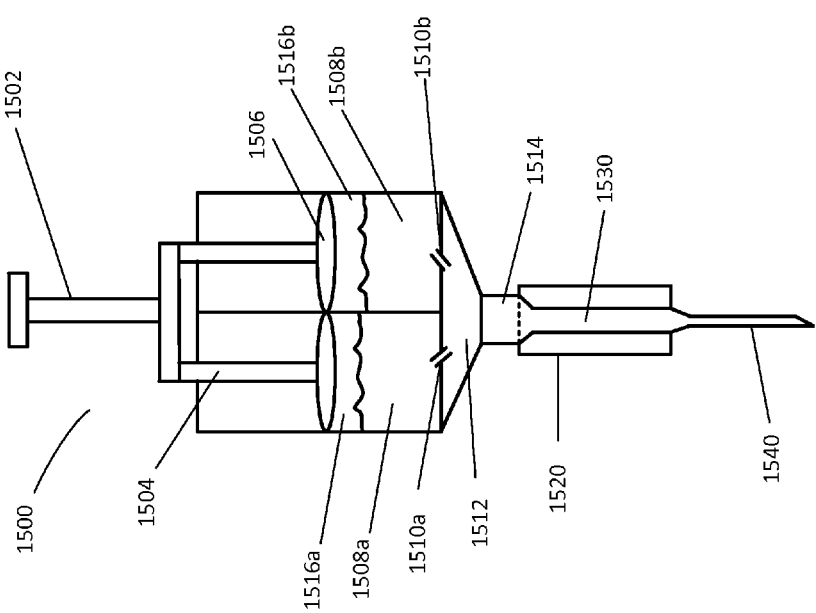

Referring to FIGS. 15A-B, a schematic of alternative embodiment system 1500 having a pair wet component containers 1516a and 1516b that contains a first wet component 1508a and a second wet component 1508b which are mixed together prior to mixing with a dry medicament component. The syringe of the system 1500 has a plunger 1502 with a pair of shafts 1504 that each drive a plunger 1506 in a respective wet component volume. As the respect wet components 1508a and 1508b are pushed through their respective valve 1510a and 1510b, the wet components mix in a wet mixing volume 1512 where a combined wet component is formed.

As the plunger 1502 is continue to push the combined wet component flows through a fluidic channel 1530 of a mixer 1520 that contains the dry medicament component. The combined medicament, which contains the dry medicament within the combined wet component, flows through the needle 1540.

While the two wet component containers 1516a and 1516b are shown the same size, it is recognize that the cross sectional area can be adjust to tailor the mixing of the two wet components. In certain embodiments that mixer 1520 and needle 1540 component can be separable from the syringe at the syringe output 1514.

Referring to FIGS. 16A-D illustrate a fluidic channel 1610 adjacent to a movable body 1608 disposed between two chambers 1604 and 1606 inside a mixing device 1600. As illustrated a wet component stored initially in chamber 1604 remains until a force moves movable body 1608 into the cavity portion of chamber 1604, which begins forcing the wet component through fluidic channel 1610, which is in a fixed position between chambers 1604 and 1606 and adjacent to movable body 1608. As previously described, the force or pressure created from movable body 1608 entering chamber 1604 is what causes a one-way opening to be forced upon and the wet component to flow through the fluidic channel. A dry medicament may be deposited near the entry, throughout or in pockets of the fluidic channel 1610 and combine with the wet component to form a wet medicament.

Figures 16A, 16B:
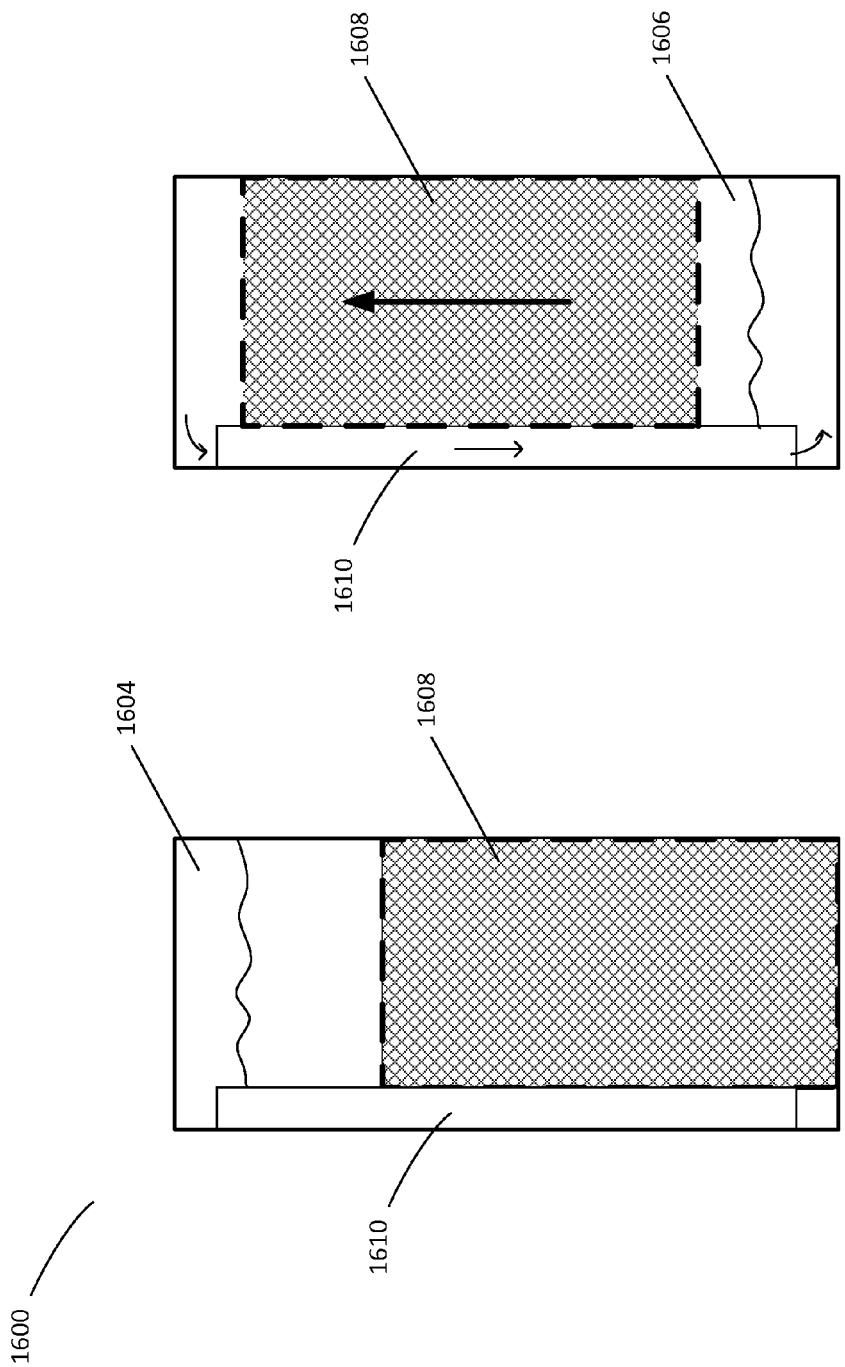
FIGS. 16 A-D illustrate a fluidic channel adjacent a movable body disposed between two chambers.
Figure 16D:
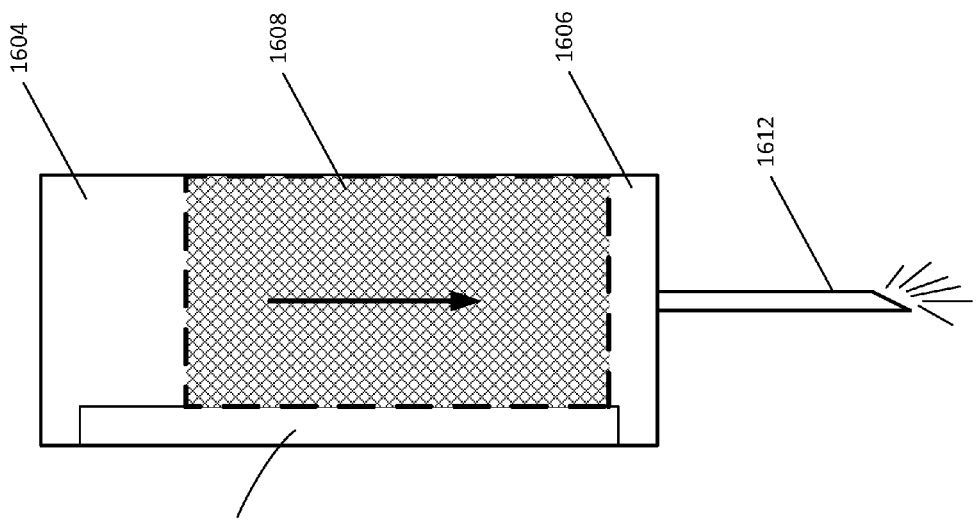
Figure 16C:
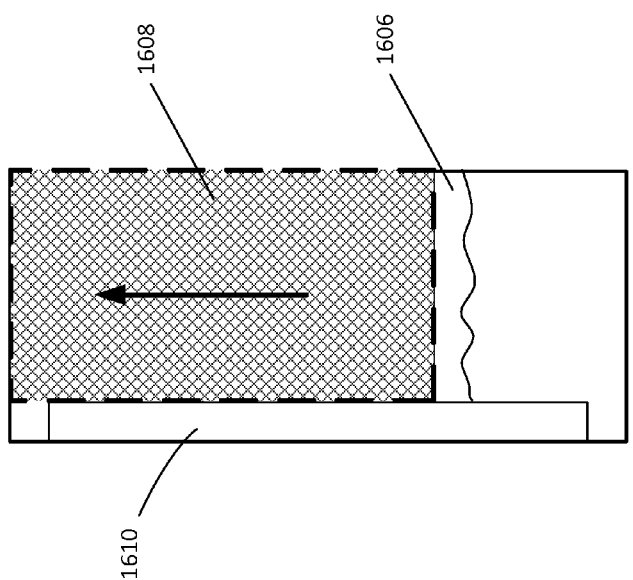

FIG. 16B illustrates the flow from 1604 through 1610 into 1606. Once a majority of the wet component has been forced out of 1604 and combined into chamber 1606, movable body 1608 may again be actuated to force the wet medicament through a needle assembly 1612 into a user or patient. Again a one way opening between the fluidic channel and 1604 and possibly a second one-way channel between 1606 and 1610 prevents the wet medicament from reentering 1604 and thus forces it through needle assembly 1612 as shown in FIG. 16D.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed:

1. A drug mixing system comprising:
   a housing comprising a first and second chamber, wherein the first chamber is configured to store a wet component;
   a movable body disposed between the first and second chambers, the movable body further comprising:
      a fluidic channel being disposed therein and configured to allow fluid communication between the first and second chamber; and
         a dry medicament being contained within the fluidic channel; and
   an actuation device configured to cause a portion of the movable body to enter a portion of the first and second chambers, the entrance of the movable body into a portion of the first and second chambers creating fluid communication between the fluidic channel and the first and second chambers, thereby forcing a portion of the wet component from the first chamber through the fluidic channel into the second chamber.

2. The drug mixing system of claim 1, wherein the second chamber is configured to store a second wet component.

3. The drug mixing system of claim 2, wherein the first and second wet components are comprised of either an acid or base.

4. The drug mixing system of claim 3, wherein when the first and second wet components combine to help dissolve the dry medicament.

5. The drug mixing system of claim 1, wherein the fluid communication caused by the actuation device results in the wet component in the first chamber and the dry medicament component in contact with the fluidic channel to combine.

6. The drug mixing system of claim 1, further comprising a needle assembly in fluid communication with the second chamber.

7. The drug mixing system of claim 5, wherein a second actuation device causes combined wet and dry medicament components to pass from the second chamber and through the needle assembly.

8. The drug mixing system of claim 1, further comprising a telescoping component attached to the housing, and whereby an extension of the telescoping component causes the actuation device to actuate.

9. The drug mixing system of claim 1, further comprising an unfolding component attached to the housing, and whereby an unfolding of the unfolding component causes the actuation device to actuate.

10. The fluidic channel of claim 1, further comprising a plurality of grooves formed in a portion of a sidewall of the fluidic channel.

11. A drug mixing and delivery system comprising:
    a housing comprising a first and second chamber, wherein the first chamber is configured to store a wet component;
    a movable body disposed between the first and second chambers, the movable body further comprising:
       a fluidic channel being disposed therein and configured to allow fluid communication between the first and second chambers; and
       a dry medicament provided within the fluidic channel;
    a first actuation device configured to cause a portion of the movable body to enter a portion of the first and second chambers, creating fluid communication between the fluidic channel and the first and second chambers, thereby forcing a portion of the wet component from the first chamber through the fluidic channel into the second chamber;
    a delivery assembly at least partially disposed in the housing; and
    a second actuation device and whereupon activation causes the movable body to enter into a portion of the second chamber, creating a fluid communication between the second chamber and the delivery assembly and forcing the combined wet component and dry medicament through the delivery assembly.

12. The drug mixing and delivery system of claim 11, further comprising an extension component incorporated into the housing and configured to increase the effective length of the housing.

13. The drug mixing and delivery system of claim 12, wherein the extension component is a telescoping component.

14. The drug mixing and delivery system of claim 12, wherein the extension component is an unfolding component.

15. The drug mixing and delivery system of claim 12, wherein an extension extending from the extension component causes the first actuation device to actuate.

16. The drug mixing and delivery system of claim 11, further comprising a safety configured to enable the second actuation device to be actuated when the safety is placed in a ready position.

17. The drug mixing and delivery system of claim 11, wherein the first actuation device is comprised of a pre-loaded spring.

18. A drug mixing and delivery system comprising:
    a housing comprising a first and second chamber, wherein the first chamber is configured to store a wet component;
    a movable body disposed between the first and second chambers, the movable body further comprising:
       a fluidic channel being disposed therein and configured to allow fluidic communication between the first and second chambers;
       a dry medicament provided within the fluidic channel; and
       wherein the fluidic channel has one or more features contained therein forming a mixing assembly;
    a first actuation device configured to cause a portion of the movable body to enter a portion of the first and second chambers, creating fluid communication between the fluidic channel and the first and second chambers, thereby forcing a portion of the wet component from the first chamber through the fluidic channel into the second chamber;
    a delivery assembly at least partially disposed in the housing; and
    a second actuation device and whereupon activation causes the movable body to enter into a portion of the second chamber, creating a fluid communication between the second chamber and the delivery assembly and forcing the combined wet component and dry medicament through the delivery assembly.

19. The drug mixing and delivery system of claim 18, wherein the one or more features include one or more features selected from a group consisting of:
    a plurality of grooves;
    bends in the fluidic channel; and
    one or more obstructions along the length of the fluidic channel.

* * * * *